US012758337B2

(12) United States Patent
Mahoney et al.

(10) Patent No.: US 12,758,337 B2
(45) Date of Patent: Oct. 13, 2026

(54) GROUNDED VIRTUAL PORTAL FOR ROBOTIC MEDICAL SYSTEM

(71) Applicant: Intuitive Surgical Operations, Inc., Sunnyvale, CA (US)

(72) Inventors: Richard Mahoney, Los Altos, CA (US); Ryan C. Abbott, San Jose, CA (US); Mitchell Doughty, Mountain View, CA (US); Govinda Payyavula, Sunnyvale, CA (US); Andrej Simeunovic, Stanford, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 140 days.

(21) Appl. No.: 18/784,169

(22) Filed: Jul. 25, 2024

(65) Prior Publication Data

US 2025/0032206 A1 Jan. 30, 2025

Related U.S. Application Data

(60) Provisional application No. 63/516,478, filed on Jul. 28, 2023.

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/76* (2016.02); *A61B 34/77* (2016.02); *A61B 90/37* (2016.02);
(Continued)

(58) Field of Classification Search
CPC ......... A61B 34/35; A61B 34/76; A61B 34/77; A61B 34/37; A61B 34/74; A61B 34/30;
(Continued)

(56) References Cited

U.S. PATENT DOCUMENTS

2004/0143176 A1* 7/2004 Foxlin ................ G01C 21/1652
2015/0018841 A1* 1/2015 Seo ........................ A61B 34/77
(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Ellis B. Ramirez
(74) *Attorney, Agent, or Firm* — Foley & Lardner LLP

(57) ABSTRACT

A grounded virtual portal to interface with a robotic medical system is provided. The system can include an input controller coupled to a first structure via a plurality of linkages. The first structure can be mechanically coupled to a base structure. The input controller can control an object of a medical environment. A head mounted display can be coupled to a second structure extending the base structure. The head mounted display can be configured to render an extended reality environment corresponding to the medical environment. A processor can establish a grounded reference frame for the input controller to be maintained in the extended reality environment rendered via the head mounted display, and configure, based on the plurality of linkages and the grounded reference frame, a force scaler function for bidirectional force delivery between the input controller and the object of the medical environment.

25 Claims, 23 Drawing Sheets

(51) Int. Cl.
*A61B 90/00* (2016.01)
*G06F 3/01* (2006.01)
*G06T 7/20* (2017.01)

(52) U.S. Cl.
CPC .............. *G06F 3/011* (2013.01); *G06F 3/016* (2013.01); *G06T 7/20* (2013.01); *A61B 2090/365* (2016.02); *G06T 2207/30004* (2013.01); *G06T 2207/30196* (2013.01)

(58) Field of Classification Search
CPC .............. A61B 90/37; A61B 2090/365; A61B 2090/372; G06F 3/011; G06F 3/016; G06T 7/20; G06T 2207/30004; G06T 2207/30196
USPC .......................... 700/264, 245; 345/427, 7, 8
See application file for complete search history.

(56) References Cited

U.S. PATENT DOCUMENTS

| | | | | |
|---|---|---|---|---|
| 2018/0250086 | A1* | 9/2018 | Grubbs | A61B 34/35 |
| 2020/0360097 | A1* | 11/2020 | DiMaio | A61B 34/35 |
| 2021/0031358 | A1* | 2/2021 | Sakaino | B25J 3/00 |
| 2021/0369365 | A1* | 12/2021 | Goswami | A61B 90/37 |
| 2022/0142711 | A1* | 5/2022 | Nguyen | A61B 17/1703 |
| 2023/0064265 | A1* | 3/2023 | Sweeney | A61B 34/35 |
| 2023/0181263 | A1* | 6/2023 | Reimer | A61B 34/20 |
| 2023/0329818 | A1 | 10/2023 | Hares | |
| 2024/0366238 | A1* | 11/2024 | Kay | A61B 17/1622 |
| 2025/0339223 | A1* | 11/2025 | Khalifa | A61B 90/20 |

* cited by examiner

250

560

550

600

700

800

900

1000

1030

1060

1400

1450

1700

GROUNDED VIRTUAL PORTAL FOR ROBOTIC MEDICAL SYSTEM

CROSS-REFERENCE TO RELATED APPLICATION

This application claims the benefit of priority under 35 U.S.C. § 119 to U.S. Provisional Patent Application No. 63/516,478, filed Jul. 28, 2023, which is hereby incorporated herein by reference in its entirety.

BACKGROUND

Surgical procedures can involve capturing imagery such as video feeds from a variety of viewpoints. In some instances, at least part of the surgical procedure can be performed with a computer-assisted robotic medical system and use of imaging devices, cameras and sensors to gather data. The data can be processed in various ways.

SUMMARY

This technical solution is directed to a grounded virtual portal for robotic medical systems. For example, it can be challenging to provide an effective extended reality experience using a head mounted display to perform a medical procedure using a robotic medical system due to the lack of reliable user interface controllers, which can impact the performance of the medical procedure by introducing delays, excessive energy consumption, or excessive kinematic movements, for example.

Systems, methods, and apparatus of this technical solution provide input controllers that are grounded or fixed and can be used in conjunction with an extended reality experience delivered via a head mounted display. The head mounted display can include one or more high resolution displays to render the extended reality experience and provide a more immersive and interactive experience for intraoperative surgery while maintaining a grounded controller interaction that can facilitate both telemanipulation and telemobility tasks in extended reality. Thus, and in some implementations, this technical solution can provide an extended reality environment via a head mounted display that is grounded or supported by a structure along with controllers that are grounded or supported by a structure, which can be used by surgeons for full peri-operative use cases that utilize a robotic medical system (e.g., including pre-operative, intraoperative, and post-operative medical procedures), collaborative surgeries utilizing a robotic medical system with multiple robotic arms or medical tools, training, teleproctoring, remote case observation, or virtual-reality-based design explorations.

At least one aspect is directed to a system. The system can be a grounded virtual portal system to interface with a robotic medical system. The system can include one or more processors, coupled with memory. The one or more processors can detect, via one or more sensors, an engagement with a head mounted display coupled to a first structure at a first position. The one or more processors can determine, via the one or more sensors responsive to detection of the engagement, a second position of one or more input controllers coupled to a second structure. The one or more input controllers can be configured to control a medical tool of the robotic medical system. The one or more processors can establish, based on the first position and the second position, a grounded reference frame for the one or more input controllers to be maintained in an extended reality environment rendered via the head mounted display. The one or more processors can configure, based on the grounded reference frame, a scaling function to translate interactions with the one or more input controllers to commands that control at least one of manipulation or movement of the medical tool of the robotic medical system.

At least one aspect is directed to a method. The method can be a method of interfacing between a grounded virtual portal system and a robotic medical system. The method can include detecting, by the grounded virtual portal system, via one or more sensors, an engagement with a head mounted display coupled to a first structure at a first position. The method can include determining, by the grounded virtual portal system, via the one or more sensors responsive to detection of the engagement, a second position of one or more input controllers coupled to a second structure. The one or more input controllers can be configured to control a medical tool of the robotic medical system. The method can include establishing, by the grounded virtual portal system, based on the first position and the second position, a grounded reference frame for the one or more controllers to be maintained in an extended reality environment rendered via the head mounted display. The method can include configuring, by the grounded virtual portal system based on the grounded reference frame, a scaling function to translate interactions with the one or more input controllers to commands that control at least one of manipulation or movement of the medical tool of the robotic medical system.

At least one aspect is directed to a non-transitory computer-readable medium storing processor executable instructions to interface between a grounded virtual portal system and a robotic medical system that, when executed by one or more processors, can cause the one or more processors to detect, via one or more sensors, an engagement with a head mounted display coupled to a first structure at a first position. The instructions, when executed by the one or more processors, can cause the one or more processors to determine, via the one or more sensors responsive to detection of the engagement, a second position of one or more input controllers coupled to a second structure. The one or more input controllers can be configured to control a medical tool of the robotic medical system. The instructions, when executed by the one or more processors, can cause the one or more processors to establish, based on the first position and the second position, a grounded reference frame for the one or more controllers to be maintained in an extended reality environment rendered via the head mounted display. The instructions, when executed by the one or more processors, can cause the one or more processors to configure, based on the grounded reference frame, a scaling function to translate interactions with the one or more input controllers to commands that control at least one of manipulation or movement of the medical tool of the robotic medical system.

At least one aspect is directed to a system. The system can include one or more input controllers coupled to a first structure that is mechanically coupled to a base structure. The one or more input controllers can be configured to control a virtual medical tool of a virtual robotic medical system rendered in an extended reality environment. The system can include a head mounted display coupled to a second structure that extends from the base structure. The head mounted display can include a camera oriented towards the one or more input controllers. The one or more processors can be configured to receive a visual data feed captured by the camera. The one or more processors can apply a hand tracking function to the visual data feed to detect an interaction with the one or more input control. The one or more processors can generate, based on the interaction detected via application of the hand tracking function, an instruction to control at least one of manipulation or movement of the virtual medical tool of the virtual robotic medical system rendered in the extended reality environment.

At least one aspect is directed to a method. The method can include providing one or more input controllers coupled to a first structure that is mechanically coupled to a base structure, the one or more input controllers configured to control a virtual medical tool of a virtual robotic medical system rendered in an extended reality environment. The method can include providing a head mounted display coupled to a second structure that extends from the base structure. The head mounted display can include a camera oriented towards the one or more input controllers. The method can include receiving, by one or more processors, a visual data feed captured by the camera. The method can include applying, by the one or more processors, a hand tracking function to the visual data feed to detect an interaction with the one or more input control. The method can include generating, by the one or more processors, based on the interaction detected via application of the hand tracking function, an instruction to control at least one of manipulation or movement of the virtual medical tool of the virtual robotic medical system rendered in the extended reality environment.

At least one aspect is directed to a system. The system can include one or more controllers coupled to a first structure that is mechanically coupled to a base structure. The one or more controllers can include an actuator to move the one or more controllers. The system can include a head mounted display coupled to a second structure that extends from the base structure. The system can include one or more processors configured to receive multi-channel data feed of a medical procedure performed via a physical robotic medical system comprising a physical medical tool. The one or more processors can generate, from the multi-channel data feed, an extended reality environment comprising a virtual robotic medical system corresponding to the physical robotic medical system and a virtual medical tool corresponding to the physical medical tool. The one or more processors can generate, from the multi-channel data feed, a force feedback stream. The one or more processors can play a video stream of the multi-channel data feed via the extended reality environment rendered by the head mounted display. The one or more processors can control the actuator of the one or more controllers in accordance with the force feedback stream and in synchronization with the video stream played by the head mounted display.

At least one aspect is directed to a method. The method can include providing one or more controllers coupled to a first structure that is mechanically coupled to a base structure. The one or more controllers can include an actuator to move the one or more controllers. The one or more controllers can provide a head mounted display coupled to a second structure that extends from the base structure. The method can include receiving, by one or more processors coupled with memory, a multi-channel data feed of a medical procedure performed via a physical robotic medical system comprising a physical medical tool. The method can include generating, by the one or more processors from the multi-channel data feed, an extended reality environment comprising a virtual robotic medical system corresponding to the physical robotic medical system and a virtual medical tool corresponding to the physical medical tool. The method can include generating, by the one or more processors from the multi-channel data feed, a force feedback stream. The method can include playing, by the one or more processors, a video stream of the multi-channel data feed via the extended reality environment rendered by the head mounted display. The method can include controlling, by the one or more processors, the actuator of the one or more controllers in accordance with the force feedback stream and in synchronization with the video stream played by the head mounted display.

These and other aspects and implementations are discussed in detail below. The foregoing information and the following detailed description include illustrative examples of various aspects and implementations and provide an overview or framework for understanding the nature and character of the claimed aspects and implementations. The drawings provide illustration and a further understanding of the various aspects and implementations and are incorporated in and constitute a part of this specification. The foregoing information and the following detailed description and drawings include illustrative examples and should not be considered as limiting.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings.

DETAILED DESCRIPTION

Figure 1:
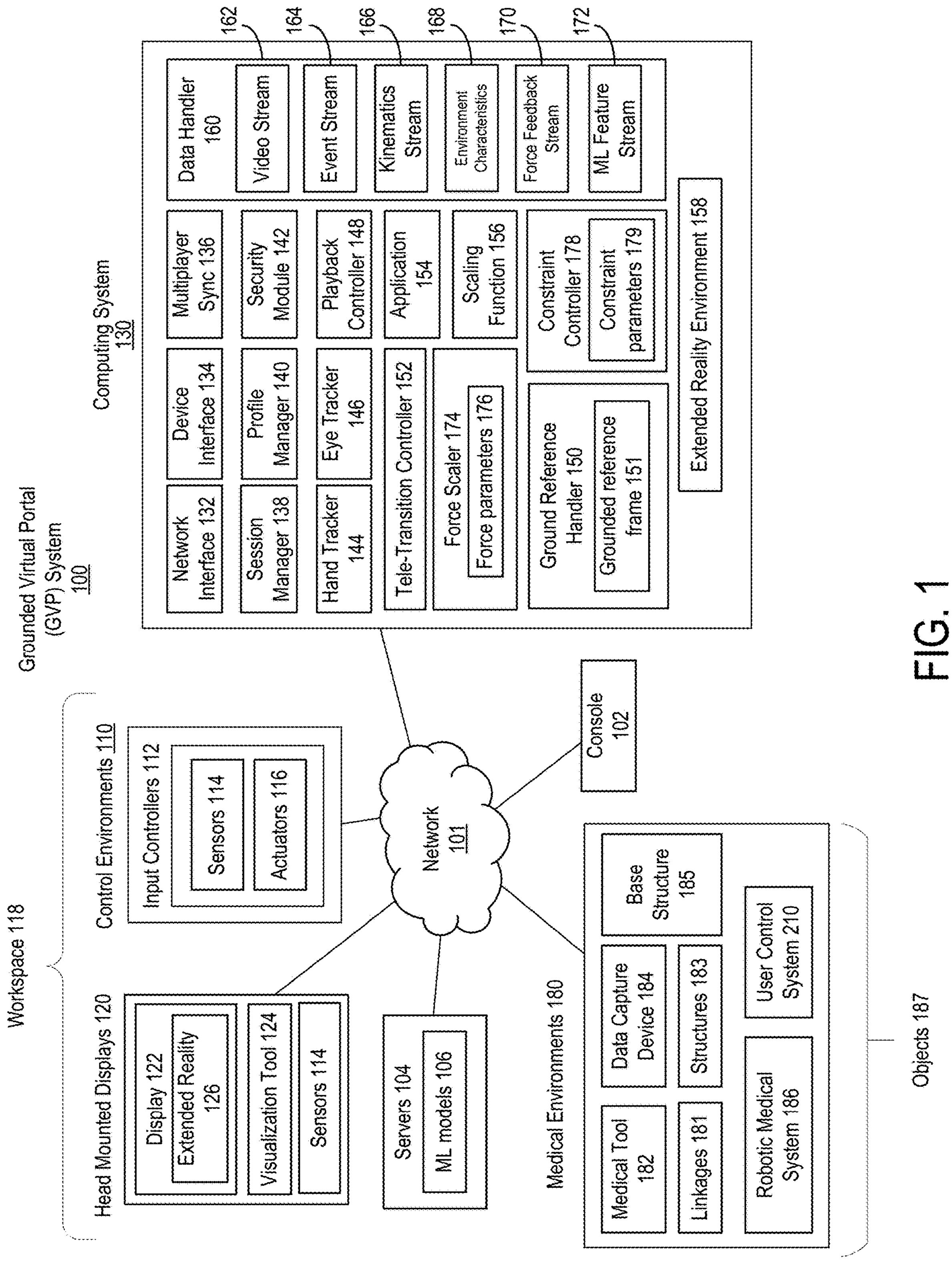
FIG. 1 depicts an example system using a grounded virtual portal (GVP) system to perform remote medical procedures, in accordance with embodiments of the present solution.

Following below are more detailed descriptions of various concepts related to, and implementations of, methods, apparatuses, and systems of a grounded virtual portal for a robotic medical system. The various concepts introduced above and discussed in greater detail below can be implemented in any of numerous ways.

Although the present disclosure is discussed in the context of a surgical procedure, in some embodiments, the present disclosure can be applicable to other medical sessions or environments or activities, as well as non-medical activities where removal of irrelevant information is desired.

This technical solution is directed to a grounded virtual portal for robotic medical systems. When performing intraoperative medical procedures, it can be challenging to provide an effective extended reality experience using a head mounted display that allows for the medical procedure to be performed without impacting the performance of the medical procedure by introducing delays, excessive energy consumption, or excessive kinematic movements, for example. To address these or other technical challenges, systems, methods, and apparatus of this technical solution provide input controllers that are grounded or fixed and can be used in conjunction with an extended reality experience delivered via a head mounted display. The head mounted display may or may not be grounded or fixed to structures or linkages to which the input controllers are fixed. The head mounted display can include one or more high resolution displays to render the extended reality experience and provide a more immersive and interactive experience for intraoperative surgery while maintaining a grounded controller interaction that can facilitate both telemanipulation and telemobility tasks in extended reality. Thus, and in some implementations, this technical solution can provide an extended reality environment via a head mounted display that may or may not be grounded or supported by a structure along with controllers that are grounded or supported by a structure, which can be used by surgeons for full peri-operative use cases that utilize a robotic medical system (e.g., including pre-operative, intraoperative, and post-operative medical procedures), collaborative surgeries utilizing a robotic medical system with multiple robotic arms or medical tools, training, teleproctoring, remote case observation, or virtual-reality-based design explorations.

In an illustrative example, a surgeon can engage a head mounted display by inserting their head into the head mounted display. The head mounted display, upon detecting the engagement of the surgeon's head or other instruction, indication or command, can establish an alignment or grounded reference with one or more grounded or fixed input controllers. The fixed head position can contribute to an intuitive alignment and facilitate maintaining the surgeon's focus on a surgical task, thereby improving the performance of the surgical task. For example, the system can perform an on-boarding or grounding process in which one or more sensors can locate the position of the grounded controllers and establish a reference frame in the extended reality environment that maintains the location of the grounded controllers. The reference frame can be established once the surgeon's head is placed into the fixed HMD. The reference frame can correspond to various aspects, including, for example, a visual reference frame, an oral or audio reference frame, or a control reference frame. The grounded reference frame can correspond to various perspectives or viewpoints, including, for example: i) a headrest sensor-based viewpoint-control with the grounded head mounted display; ii) a grounded reference frame corresponding to a physical object in the medical environment; or iii) a grounded reference corresponding to a virtual object placed in the medical environment.

To detect input in the extended reality environment, the head mounted display can include a camera that can track the movement of the grounded input controllers. In some cases, the grounded input controllers can include sensors that can detect an input instead of, or in addition to, the cameras that can track hand movement of the grounded input controllers. To convert the detected inputs into commands for controlling a medical tool of a robotic medical system, this technical solution can utilize a scaling function that can translate the motions of the input controller to corresponding motions of the medical tool without introducing unnecessary or excessive tremor or noise, while allowing for efficient movement in a smaller workspace volume to correspond to a task performed in the medical surgery. By providing grounded input controllers that can interact with a robotic medical system via an extended reality environment delivered through an immersive head mounted display, this technical solution can facilitate creating a connection to the surgeon's neuromotor system so that an extended physiological proprioceptive connection can made in telepresence, thereby improving the performance of the medical procedure without causing excessive delays, energy consumption, or other inefficiencies.

In addition to telemanipulation of the robotic medical system, this technical solution can provide a tele-mobility experience with telepresence in which the user can use the grounded controller inputs to navigate movement from a physically seated position in a console to a moving virtual experience in an extended reality, 3-dimensional space. By using the grounded head mounted display and grounded input controllers, this technical solution can maintain a hand-eye orientation or reference frame during the extended reality experience, thereby improving the performance of the medical procedure.

In addition to tele-mobility, this technical solution can provide for tele-navigation, in which the user can navigate in 3-dimensions and with 6 degrees of freedom in an extended reality environment. For example, using the grounded head mounted display and grounded input controllers, this technical solution can function as a telenavigator for medical tool guidance (e.g., catheters or endoscopes).

This technical solution can be applied in various medical contexts, including for example, peri-operative procedures, training, teleproctoring, remote case observation, virtual reality-based design explorations, or virtual reality meetings. In an illustrative example, a console of this technical solution can be placed in the office of a surgeon in order to practice cases, engage in telementoring experiences or teleproctoring experiences, or attend events in an extended reality environment. In another illustrative example, the console of this technical solution can be portable and brought to other locations to demonstrate or perform the various use cases, including playing recorded or captured medical procedures.

To playback medical procedures, this technical solution can construct a multi-channel file format for multi-modal streams of data captured or generated during a medical procedure. The file format can include, for example, a video stream (e.g., video captured by cameras in the operating room or on a medical tool such as an endoscope), an event stream (e.g., medical tool installation events), environment characteristics (e.g., tissue or body cavity information), kinematics stream (e.g., position and motion of the medical tool), a force feedback stream (e.g., forces detected by the medical tool indicating of soft or hard tissue), or a feature stream generated by a model trained with machine learning (e.g., predictions of task or phase of the medical procedure generated based on data sensed or captured during the medical procedure). The data can be synchronized across the multiple channels using timestamps or other features. The technical solution can playback the medical procedure in the extended reality environment delivered by the head mounted display while providing force feedback via actuators of the input controllers such that the user can feel or experience a full spectrum of the medical procedure.

The grounded virtual portal of system can, in some cases, provide for a ground-able system that can refer to or include a system that is in between a free-flowing VR systems and a grounded console system. A ground-able virtual portal system can allow for mobility around an environment. In a ground-able GVP system, the HMD can be detachable from a mount, linkage, or other structure. When the HMD is detached or decoupled from a structure, the GVP system of this technical solution can switch to an AR mode. The GVP system of this technical solution can allow for switching between AR and VR modes, in association with whether the HMD is grounded (attached) or not (detached), by adjusting, tuning, calibrating or otherwise establishing the video, movement, or bidirectional conveyance of force based on a scaling function, force scalar function or reference frames. Further, the experience provided via XR can be personalized or customized based on a usage situation, a user profile, or how the HMD or input controller is grounded.

FIG. 1 depicts an example grounded virtual portal (GVP) system 100, in accordance with implementations. The GVP system 100 can include one or more consoles 102, computing system 130, servers 104, control environments 110, head mounted displays (HMDs) 120, and medical environments 180 communicating or interacting with each other over a network 101. The grounded virtual portal system 100 can include one or more components, systems, or functionality depicted in FIG. 1. Each server 104 can include one or more machine learning (ML) models 106. Each control environment 110 can include input controllers 112 that can include one or more sensors 114 and actuators 116. In some cases, the control environment 110 can refer to or include a flat top surface, desk, table or flap on which a virtual input controller 112 can be provided, and input can be sensed by the computing system 130 via a hand tracker 146. Each HMD 120 can include one or more visualization tools 124, sensors 114 and displays 122 that can display extended reality 126. A control environment 110 and an HMD 120 can be used together, or form, provide or depict a workspace 118. Each medical environment 180 can include one or more medical tools 182, data capture devices 184, robotic medical systems 186 and user control systems 210. Each computing system 130 can include one or more network interfaces 132, device interfaces 134, multiplayer syncs 136, session managers 138, profile managers 140, security modules 142, hand trackers 144, eye trackers 146, playback controllers 148, ground reference handlers 150, tele-transition controllers 152, applications 154, scaling functions 156 and extended reality environments 158. computing system 130 can include one or more data handlers 160, each one of which can include one or more video streams 162, event streams 164, kinematics streams 166, environment characteristics 168, force feedback streams 170 and ML feature streams 172. computing system 130 can include one or more force scalers 174 with one or more force parameters 176. computing system 130 can include one or more constraint controllers 178 with one or more constraint parameters 179.

The input controllers 112 can be grounded or mechanically coupled to a structure via a boom-mount, a cart-mount, or a floor mount system, or other type of linkage or structural component. In some implementations, the computing system 130 can include an articulated forearm rest with an integrated hand controller 112.

In some cases, the computing system 130 can provide a virtual, grounded hand controller as an input controller 112. The virtual, grounded hand controller can be represented in extended reality as a point cloud or dot cloud in an operating room scene and provide the ability to manipulate controllers in the extended reality environment or medical environment.

System 100 can include workspace 118. Workspace 118 can include a region or a volume of space within which a user performs a particular medical operation (e.g., a surgery). Workspace 118 can include a physical workspace or a virtual or augmented representation of a volume of space within which a medical procedure or a treatment (e.g., a surgery) is performed. Workspace 118 can correspond to an area within which medical tools 182 have a freedom or range of movement, allowing the user to perform the operation.

Workspace 118 can correspond to, or include, a location or an area in which a user can access or use a head mounted display (HMD) 120. For example, workspace 118 can include an office, a cleanroom, or a location comprising control environment 110 and a head mounted display (HMD) 120. Workspace 118 can include, or be included within, a medical environment 180. Control environment 110 can include a workstation (e.g., a desk) that can provide a stationary (e.g., grounded or attached to a desk) HMD 120 which a user (e.g., a medical professional, such as a surgeon) can wear or insert their head. Control environment 110 can include one or more input controllers 112 (e.g., sensors 114 and actuators 116) which the user can handle, operate or use to use, control or move medical tools 182, robotic medical systems 186 or data capture devices 184 in a physical medical environment 180, via a network 101.

The workspace 118 can include an HMD 120 in which the user can insert or fit their head. HMD 120 can be a part of, attached to, or coupled with a set location and therefore be locked, stable, or grounded to a particular position. Input controllers 112 (e.g., sensors 114 and actuators 116) can be provided in the workspace 118 (e.g., at the workstation in front of, near or beneath the grounded HMD 120, allowing the user to participate in the medical procedure taking place in the medical environment 180 remotely. HMD 120 can have a feature (e.g., a handle, a holder, or a bar) that is attached to, mounted on, or otherwise held in place to a particular location, such as, a desk at a workspace 118 in which the user (e.g., a surgeon) utilizes a HMD 120 to participate in a surgery via the network 101 and using the computing system 130. The HMD 120 can be worn while the user is moving around (i.e., HMD 120 is not fastened to, linked to, or locked to the system). The HMD 120 may also be worn by the user when it is locked, removably attached or linked to the system, and then the HMD 120 can be unlocked, detached or disconnected from the system, and vice versa. The HMD 120 can be grounded or mechanically coupled to a structure via a boom-mount, a cart-mount, or a floor mount system, or other type of linkage or structural component.

In a ground-able GVP system, the HMD 120 can be detachable from the mount, linkage, or other structure. When the HMD 120 is detached or decoupled from a structure, the GVP system 100 of this technical solution can switch to an AR mode. For example, the tele-transition controller 152 can detect that the HMD 120 is decoupled from a fixed structure or is no longer in the grounded state, and then automatically transition to another viewing mode, such as AR in which some level of see-through is provided or a pass-through real-time video feed is provided.

HMD 120 can be used to display to the user (e.g., via display 122 of the HMD 120) extended reality 126. Artificial reality, virtual reality, actual or physical reality, or any type of mixed reality, such as any mixture of artificial reality, virtual reality, actual or physical reality, may all be forms of content that the HMD 120 receives from the system 100, which may be referred to as extended reality (XR). Extended Reality (XR) is a term encapsulating augmented reality (AR), virtual reality (VR), mixed Reality (MR) and everything in between. Extended reality 126 can include any combination of physical, virtual, actual or artificial features that can be presented for display to the user. Extended reality 126 can include an extended reality (e.g., physical, virtual, actual or artificial) representation, illustration or rendering of the medical environment 180, or any feature or detail within it. Extended reality 126 can include an XR representation of medical tools 182, data capture devices 184, robotic medical systems 186, as well as any persons in the medical environment 180 (e.g., doctors, nurses and patient), along with locations of the medical tools 182 with respect to the patient or any other reference point in the medical environment 180.

According to one aspect, the user wearing the HMD 120 can have their location, orientation, and/or gaze direction detected by the HMD 120, and the system 100 can be informed of their detected location and gaze direction (e.g., via eye tracker 146). In accordance with the detected location, orientation, and/or gaze direction, the system 100 can determine a view of the content inside the space (e.g., virtual) of the content and then produce an image showing that view. The HMD 120 can receive the image from the system 100 for rendering. Images can include images from various data capture devices 184 (e.g., cameras or microphones) providing data for creating an extended reality environment 158 illustrating, depicting or otherwise duplicating the medical environment 180 in real time for its display as extended reality 126 at the user's HMD 120.

In some implementations, the HMD 120 contains or corresponds to an electronic component that can be worn by a user and can deliver or display to the user any kind and form of mixed reality, artificial reality, or virtual reality experience. To give the user an experience of artificial reality, the HMD 120 can render one or more images, videos, audios, or combinations of these. In some implementations, audio is delivered by an external device (such as speakers and/or headphones) that receives audio data from the HMD 120, the system, or both and then outputs audio based on that data. The HMD 120 may comprise sensors, a communication interface, an image renderer, and/or an electronic display 122 in some example. HMD 120 can include a visualization tool 124 that can utilize data from various sensors 114 (e.g., images or illustrations) to create visual representations of the extended reality 126 to be displayed to the user. For example, the visualization tool 124 can include a renderer to render multiple images of the medical environment 180 from various angles and generate a current representation of one or more features or details in the medical environment.

HMD 120 can include sensors 114, a communication interface, visualization tool 124 and/or an electronic display (e.g., display 122). These components can operate together to detect a location and an orientation of the HMD 120, and/or a gaze direction of the user wearing the HMD 120, and can render an image of a view within the virtual, artificial, physical or mixed reality corresponding to the detected location and the orientation of the HMD 120, and/or the gaze direction of the user.

In some implementations the HMD 120 can include force sensors 114 on the boundaries of the grounded head-mounted display (e.g., left, right, top, and bottom) to translate force to movement and allow a user to independently control their head pose in an extended reality scene. For example, the head can remain fixed and the HMD, using the sensors 114 mounted on the boundaries, can detect or sense pressure applied to the grounded HMD by the user's face. Responsive to detecting this pressure or force, the HMD can re-orient the user's virtual camera or otherwise control aspects of the computing system 130.

A location, such as a location of a medical tool 182 in a medical environment 180, the orientation of the HMD 120, and/or the user's gaze direction inside the HMD 120 can all be detected by the sensors 114 in various implementations. Sensors 114 can include electronic or electrical components, a combination of electronic and software components, mechanical or electromechanical components, or any combination thereof. Various sensors 114 can include devices, systems or components detecting, measuring and/or monitoring a variety of signals in a variety of applications, such as temperature, pressure, location, proximity, light, humidity, motion, acceleration, velocity, distance, magnetic field, electric field, pressure or movement of gas, images (e.g., camera), sounds (e.g., microphone), force, touch, moisture, radiation, pH, humidity or vital signs of a person. For instance, a sensor 114 can include a global positioning system sensor or transceiver for location, one or more image sensors for capturing images, one or more accelerometers, one or more gyroscopes, one or more magnetometers, or another suitable form of sensor that detects motion and/or location. For instance, one or more gyroscopes can detect rotational movement (e.g., pitch, yaw, roll) and one or more accelerometers can measure translational movement (e.g., forward/back, up/down, left/right). A physical object, a user gesture, the contour of the hand, a user interaction, etc. may be detected using an image that the imaging sensors 114 can capture in some embodiments.

Actuators 116 can be used by a user (e.g., a surgeon utilizing a HMD 120 to perform a surgery, via a network 101 in a remote medical environment 180) to control movements, handling or functions of medical tools 182 or a robotic system 186. For example, actuators 116 can be used by the user to move a medical tool 182 in a particular direction by a certain amount of distance or with a certain amount of force. For example, actuator 116 can detect a soft movement of a user (e.g., a movement below a particular threshold of force in a particular direction) to emulate the same low force movement (e.g., movement with a force below the same threshold) by the medical tool 182. Actuator 116 can be used by the user to control operation and functionality of the medical tools 182, including their movement, positioning, activity or any other action.

Actuator 116 can include any device or system for detecting movement, force, and facilitating handling for user interaction with a tool or a system. Actuator 116 can include the functionality to convert electrical signals into physical motion or force, or vice versa. For instance, piezoelectric actuators can be used to utilize piezoelectric materials for precise motion, solenoid actuators can leverage electromagnetism to create linear or rotational motion, voice coil actuators (VCA) can utilize Lorentz force to detect or provide accurate movements. Linear resonant actuators can be used to produce vibration and tactile feedback to indicate resistance or force detected in the feedback. For example, rotary actuators 116 enable rotational motion, allowing joysticks to move in a circular manner, pneumatic actuators 116 can use compressed air to provide force feedback, and hydraulic actuators 116 can employ fluid pressure for similar purposes. Actuators 116 can include joysticks, foot pedals, buttons or computer mice. Actuators 116 can include gesture capturing tools (e.g., gloves with sensors 114), touchscreens or touch pads. Actuators 116 can include dials or knobs or haptic sensor feedback mechanisms.

Sensors 114 can locate a medical tool 182, a data capture device 184, a robotic medical system 186 or a HMD 120 and identify their locations, relative positions and/or orientation by detecting any combination of positional, rotational or translational movement or data. In one example, the sensors 114 can track the location of, or a translational movement and the rotational movement of a medical tool 182 or the HMD 120 in relation to its previous orientation and location with respect to a medical environment 180 and/or extended reality environment 158. For instance, the extended reality environment 158 can illustrate in virtual reality or augmented reality the medical environment 180 and display it as the extended reality 126 in display 122. By adding up or integrating the detected translational movement and/or rotational movement, the sensors 114 can then determine the medical tool's or HMD's new orientation and/or location. Assuming for the sake of illustration that the medical tool 182 or HMD 120 is oriented 25 degrees from a reference direction, the sensors 114 can decide that the medical tool 182 or HMD 120 now faces or is oriented in a direction 45 degrees from the reference direction in response to sensing that the medical tool 182 or HMD 120 has rotated 20 degrees (e.g., in either medical environment 180 or extended reality environment).

Assuming for another example that the medical tool 182 or HMD 120 was located two inches away from a reference point in a first direction (e.g., in either medical environment 180 or extended reality environment 158), in response to detecting that the medical tool 182 or HMD 120 has moved three inches in a second direction, the sensors 114 can determine that the medical tool 182 or HMD 120 is now located at a vector multiplication of the two inches in the first direction and the three inches in the second direction. In one aspect, according to the location and the orientation of the HMD 120, a gaze direction of the user can be determined or estimated. Similarly, using a gaze direction of the user at the HMD 120, a location of the medical tool 182 in the extended reality environment 158 (e.g., as illustrated in the extended reality 126 of the display 122) or medical environment 180.

In some implementations, the sensors 114 have electrical components, or electronic components and software components combined, that produce sensor 114 measurements that are related to the environment around the HMD 120. One or more sound sensors 114 (e.g., microphones), one or more imaging sensors (e.g., cameras), one or more wireless signal detectors (e.g., radio transceivers), one or more sensors used to identify the location (e.g., gyroscopes, velocity sensors or GPS sensors) and/or orientation sensors 114 of the HMD 120 are a few examples of the sensors 114 for generating sensor measurements. One configuration has each sensor 114 set to produce a sensor measurement in or on the corresponding surface. A surface could be a matching size or feature of the HMD's surrounding environment. In one instance, a microphone can pick up a sound and produce an audio signal that electrically describes the sound that was picked up. In one case, an imaging sensor 114 can capture an image corresponding to a user's view (or a view from a location of the HMD based on the HMD's orientation). In one example, a wireless signal detector can detect a nearby device based on a wireless signal received at a predefined frequency (e.g., ISM, Wi-Fi, any cellular frequency bands, or any frequency). A global positioning system sensor 114, accelerometer sensor 114 or a velocity sensor 114, for example, can determine the location of the HMD 120. Each of the outputs of these sensors 114 can be used by the computing system 130 to create an extended reality environment 158 (e.g., as a digital twin of the medical environment 180) and display it as an extended reality 126 in the display 122 of the HMD 120.

Sensors 114 can include eye tracking sensors or head tracking sensors. Eye tracking sensors 114 and head tracking sensors 114 can offer information such as locations, orientations, or gaze directions of the user's (e.g., wearer's) eyes or head. Inside out tracking cameras configured to give pictures for head tracking operations can be used in some implementations of the sensors 114. The sensors 114 can be eye tracking sensors that give eye tracking data, such example data related to at least one of the user's eyes' location or orientation. In other implementations, the sensors 114 measure eye motion optically, for example, by emitting light (e.g., infrared light) towards the eyes and detecting reflections of the emitted light. The sensors 114 can be pointed towards the user's eyes (as opposed to sensors that record images of a world outside of the HMD). In various implementations, the head tracking sensors 114 generate motion data that includes at least one of the head's position, velocity, or acceleration (e.g., of the HMD).

The sensors 114 can include hand tracking sensors. Hand tracking sensors 114 can offer information such as the positions or orientations of one or more of the user's hands. The hand tracking sensors can generate motion data that includes at least one of a hand's position, velocity, or acceleration (e.g., of a hand device operated by the hand). Any of a variety of position sensors, such as an inertial measurement unit (IMU), an accelerometer, a gyroscope, a magnetometer (e.g., magnetic compass), or any combination thereof, may be used in the head tracking sensors and hand tracking sensors. Body position sensors 114, such as leg sensors or torso sensors, can be included among the sensors.

Hand tracking data collected by sensors 114 can be improved with information about physical constraints. Physical constraints can improve the collection of hand tracking data by filtering out data that falls outside of the constraints, or improving the fidelity or resolution of data collection within certain constraints. Constraints can correspond to volumes or areas of the physical space in which a user's hands are located. Constraints can correspond to speed or frequency of movements. For example, a constraint can include a high pass frequency filter that corresponds to noise or tremor that is to be removed. Removing unwanted frequencies can improve the hand tracking data, or the performance, reliability, or action performed by the computing system 130 using or based on the hand tracking data.

Hand tracking sensors 114 can track motion in 6 degrees of freedom. Hand tracking sensor can include an optical sensor that can track an absolute position of the hand and absolute orientation of the hand. The hand tracking sensor 114 can include an inertial measurement unit ("IMU") that can track finger movement, such as a fingertip controller. The IMU can include 3 accelerometers, 3 gyroscope, and 3 magnetometers in order to track in 9 degrees of freedom. The sensors 114 can include an articulated forearm controller.

The hand tracker 144, upon obtaining data from the various hand tracking sensors 114, can perform, execute, or apply a sensor fusion technique. With the sensor fusion technique, the hand tracker 144 can track finer or hand movement with reduced drift and improved precision. For example, using a gravity vector and magnetometer, the computing system 130 can provide for improved hand tracking precision while reducing drift, thereby allowing for improved medical procedure performance.

The sensors 114 can capture images or take pictures of the area around them. For example, the sensors can capture images of an environment in or around the HMD user's field of view. The images can be representations of the environment, such as a color or grayscale array or matrix of pixels indicating light capture properties (e.g., color, brightness, intensity). The environment can be both indoors and outdoors, and it can include both natural and man-made structures, terrain, or other items such as sky, clouds, roads, buildings, streets, pedestrians, or bicycles. The environment may contain one or more things (for example, real-world objects), which can be represented by the images acquired by the sensors.

A motion detector 114 may be included in the system. The motion detector can comprise any function, operation, routine, logic, or instructions to detect and monitor movement of the user's head or hands based on sensor data received from sensors. The motion detector, for example, can receive sensor data that includes at least one of velocity or acceleration (of the head or one or more hands) and generate motion data based on the received sensor data. In response to sensor data, the motion detector can generate motion data that includes at least one of a location or an orientation. In other examples, the sensors can partially execute functionality of the motion detector, generating motion data, such as to generate the motion data using processing hardware of the sensors and provide the motion data to any computing device or processing circuitry.

The motion detector 114 can produce motion data in a specific frame of reference. For example, the motion detector can retrieve orientation data from sensor data and use it to transform sensor data to a frame of reference used by simulation generator to generate the virtual environment from which image renderer or electronic display 122 generates display images. As the HMD may provide a baseline frame of reference according to how the user experiences the simulated environment when using the HMD, the motion detector can transform the sensor data to a frame of reference corresponding to at least one of the position or orientation of the HMD.

The motion tracker 114 may include or be a hand tracker. The hand tracker can receive sensor data about one or more of the user's hands from one or more associated hand tracking sensors and create motion data based on the received sensor data, including at least one of the one or more hands' location, velocity, or acceleration. The hand tracker, for example, can receive sensor data from the hand tracking sensor that is connected with the hand device in order to determine motion data indicative of motion of a hand device (and hence the user's hand). To track the user's one or more hands, the hand tracker can keep a record of location, orientation, velocity, or acceleration data (or combinations thereof). In some examples, the hand tracker incorporates accelerometers, position sensors, and/or velocity sensors.

In some embodiments, the motion detector 114 includes a head tracker. The head tracker can receive sensor data about the user's head from one or more related head tracking sensors and generate motion data that includes at least one of the head's position, velocity, or acceleration based on the received sensor data. The head tracker, for example, can receive sensor data from the head tracking sensor that is linked with the HMD to determine motion data indicative of motion of the HMD (and hence the user's head). To track the user's head, the head tracker can keep a record of position, orientation, velocity, or acceleration data (or combinations thereof). In some examples, the head tracker includes accelerometers, position sensors, and/or velocity sensors.

Visualization tool 124 can include an image renderer that an electronic component or a combination of an electronic component and a software component that generates one or more images for display, such as in response to a change in view of the virtual reality, artificial reality, physical or mixed reality's space (e.g., extended reality 126). Visualization tool 124 can be implemented, for example, as a processor (or a graphical processing unit (GPU)) that executes instructions to accomplish the different functions described herein. Visualization tool 124 may receive data describing an image to be displayed over the communication interface and render the picture via the electronic display. The data from the system may be compressed or encoded in some implementations, and the image renderer may decompress or decode the data to generate and render the image. In one aspect, the visualization tool 124 receives the compressed image from the computing system 130 and decompresses it, thereby reducing the communication bandwidth between the system and the HMD 120. In one aspect, the process of detecting the HMD's location, orientation, and/or gaze direction, and generating and transmitting to the HMD by the system a high resolution image (e.g., 1920 by 1080 pixels) corresponding to the detected location, orientation, and/or gaze direction may be computationally exhaustive and may not be performed within a frame time (e.g., less than 10 ms).

Display 122 can include any electronic component that provides, shows an image in some implementations. Display 122 can include a liquid crystal display or an organic light emitting diode display, for example. Display 122 can be translucent, allowing the user to see through it. When a user wears the HMD 120, display 122 can be situated close (e.g., less than 3 inches) from the user's eyes. In one sense, display 122 can produce or project light into the user's eyes in accordance with the image rendered by the visualization tool 124 (e.g., image renderer). In some cases, the display 122 may not be translucent, but cameras can provide a real-time pass through optical or video feed to simulate or emulate the user seeing through the display 122.

Example system 100 can include or be associated with a medical environment 180. Medical environment 180 can include any environment directed to providing or implementing medical procedures, services or treatments. For instance, medical environment 180 can be a medical surgical environment, that can include a surgical facility such as an operating room in which a surgical procedure, whether, invasive, non-invasive, in-patient, or out-patient, can be performed on a patient.

Medical environment 180 can be a location in which any type of medical sessions or activities, can be performed. Medical environment 180 can include one or more data capture devices 184. Data capture devices 184 can collect images (e.g., for a video stream 162), kinematics data (e.g., for a kinematics stream 166), or system events (e.g., for event stream 164). For example, the data capture device 184 can include an image capture devices designed, constructed and operational to capture images from a particular viewpoint within the medical environment 180, such as locations of particular data capture devices 184, medical tools 182, robotic medical systems 186, or any locations on a ceiling or walls of an operation room. The data capture devices 184 can be positioned, mounted, or otherwise located to capture content from any viewpoint that facilitates the grounded virtual portal system 130 to perform the medical procedure.

For example, in some embodiments, a first data capture device 184 can be positioned to capture one or more images of an area where a patient is located within the medical environment 180. A second data capture device 184 can be positioned to capture one or more images of an area where one or more medical professionals are physically or virtually located within the medical environment 180. A third data capture device 184 can be configured to capture one or more images of other designated areas (e.g., physical, augmented or virtual) within the medical environment 180. The data capture devices 184 can include any of a variety of sensors, cameras, video imaging devices, infrared imaging devices, visible light imaging devices, intensity imaging devices (e.g., black, color, grayscale imaging devices, etc.), depth imaging devices (e.g., stereoscopic imaging devices, time-of-flight imaging devices, etc.), medical imaging devices such as endoscopic imaging devices, ultrasound imaging devices, etc., non-visible light imaging devices, any combination or sub-combination of the above mentioned imaging devices, or any other type of imaging devices that can be suitable for the purposes described herein.

The images that are captures by the data capture device 184 can include still images, video images, infrared images, X-ray images, vector images, bitmap images, other types of images, or combinations thereof. In some embodiments, one or more of the data capture devices 184 can be configured to capture other parameters (e.g., sound, motion, pressure, radiation or temperature) within the medical environment 180. The data capture devices 184 can capture the images at any suitable predetermined capture rate or frequency. Other settings, such as zoom settings or resolution, of each of the data capture devices 184 can vary as desired to capture suitable images from a particular viewpoint. The data capture devices 184 can have fixed locations, positions, or orientations. The data capture devices 184 can be portable, or otherwise configured to change orientation or telescope in various directions. The data capture devices 184 can be part of a multi-sensor architecture including multiple sensors 114, with each sensor 114 being configured to detect, measure, or otherwise capture a particular parameter (e.g., sound, temperature, pressure, vibration, distance, images, or any other data).

The images captured by the data capture devices 184 can be sent as a data stream component to a visualization tool 124. A data stream component can be considered any sequence of digital encoded data or analog data from a data source such as the data capture devices 184. The visualization tool 124 can be configured to receive a plurality of data stream components and combine the plurality of data stream components into a single data stream.

The visualization tool 124 can receive a data stream component from a medical tool 182. The medical tool 182 can be any type and form of tool used for surgery, medical procedures or a tool in an operating room or environment associated with or having an image capture device. The medical tool 182 can be an endoscope for visualizing organs or tissues, for example, within a body of the patient. The medical tool 182 can include other or additional types of therapeutic or diagnostic medical imaging implements. The medical tool 182 can be configured to be installed in a robotic medical system 186.

The robotic medical system 186 can be a computer-assisted system configured to perform a surgical or medical procedure or activity on a patient via or using or with the assistance of one or more robotic components or medical tools 182. The robotic medical system 186 can include one or more manipulator arms that perform one or more computer-assisted medical tasks. The medical tool 182 can be installed on a manipulator arm of the robotic medical system 186 to perform a surgical task. The images (e.g., video images) captured by the medical tool 182 can be sent to the visualization tool 124. The robotic medical system 186 can include one or more input ports to receive direct or indirect connection of one or more auxiliary devices. For example, the visualization tool 124 can be connected to the robotic medical system 186 to receive the images from the medical tool 182 when the medical tool is installed in the robotic medical system (e.g., on a manipulator arm of the robotic medical system). The visualization tool 124 can combine the data stream components from the data capture devices 184 and the medical tool 182 into a single combined data stream for presenting on a display 122 (e.g., display 330 depicted in FIG. 3). The display 122 can be associated with a device interface 134, or a display system that can be provided within the medical environment 180.

Physical objects, also referred to as objects 187, can include any objects within a medical environment 180, such as any medical tools 182, data capture devices 184, head mounted displays 120, input controllers 112, any device that can be used in a workspace 118 or medical environment 180. Objects 187 can be rendered and represented virtually as virtual objects in an extended reality environment 158 that can illustrate, represent or depict the medical environment 180 along with any objects 187 within the medical environment 180. Objects 187 can include medical tools 182 or manipulator arms for handling the medical tools 182 at the robotic medical system 186. Objects 187 can include a head mounted display 120 or a data capture device 184.

Linkages 187 can be used to link or connect together different components of the workspace 118 or the medical environment 180. Linkages 187 can include or refer to any mechanical connections or structures that join different components or systems, to allow them to physically connect, interact and function together. For instance, a linkage 187 can be any arrangement of parts that transmits physical force (e.g., push or pull) or any other movement or motion from one element (e.g., tool or system) to another. Linkages 187 can include any combination of joints, levers, clips or arms allowing connection of a medical tool 182, data capture device 184, input controller 112, head mounted display 120, user control system 210 or robotic medical system 186 with one or more structures 183 or base structure 185.

Linkages 187 can include complex assemblies designed to support and position equipment in various medical environments 180. For example, in a surgical robotic medical system 186, linkages 187 can include, or be coupled or deployed with, a boom-mount, which can include an articulated arm (e.g. comprising one or more parts) attached to a wall or ceiling and allowing flexible positioning of medical tools 182. For instance, linkages 187 can include, or be coupled or deployed with, a cart-mount, in which components can be mounted on a mobile cart that can be moved around the medical environment 180. For example, linkages 187 can include, or be coupled or deployed with, a floor-mount that can secure or mount equipment directly to the floor, providing a stable and fixed base facilitating a consistent positioning with a grounded reference frame 151 for a medical procedures.

Structures 183 can include any physical objects for providing physical support to any devices or system components. Structures 183 can be configured to provide physical support to any frameworks or components, or provide stability and positioning to various elements within a system 100. Structures 183 can include any physical framework or scaffold that supports and any features or components of a medical environment 180 or workspace 118 in place. For instance, a structure 183 can include a rigid frame, an articulated arm, or a platform that interfaces with a base structure 185 to provide a static or specific positioning and support (e.g., with respect to a grounded reference frame or a frame of reference 151). For instance, in a surgical robotic medical system 186, the first structure 183 can be an articulated arm that supports the input controller 112, allowing precise manipulation of medical tools 182 with respect to a grounded frame of reference (e.g., 151). For instance, another structure 183 can be a mounting frame that holds a head-mounted display 120 to provide a stability and positioning relative to the user's viewpoint and also with respect to the same grounded frame of reference (e.g., 151). Structures 183 can be mechanically coupled to a base structure 185, which can serve as a foundational element providing stability and anchoring for the entire system.

A base structure 185 refers to the foundational framework or support system that provides stability and anchoring for other structures and components within a system. Broadly, it can include any primary framework or platform that forms the foundation for additional elements. More precisely, a base structure can be a heavy-duty frame, a stabilized platform, or a fixed mount that ensures the entire system remains securely anchored. In a surgical robotic medical system, the base structure 185 might be a floor-mounted platform that provides a stable and immovable foundation for the surgical robot and its associated components. It could also be a cart-based system with a broad and stable base to prevent tipping and ensure smooth movement. By providing a stable foundation, the base structure 185 ensures that all attached components, such as input controllers and head-mounted displays, maintain their positions and functions accurately during surgical procedures, enhancing overall system reliability and precision.

Network 101 can be any type or form of network. The geographical scope of the network 101 can vary widely and can include a body area network (BAN), a personal area network (PAN), a local-area network (LAN) (e.g., Intranet), a metropolitan area network (MAN), a wide area network (WAN), or the Internet. The topology of the network 101 can assume any form such as point-to-point, bus, star, ring, mesh, tree, etc. Network 101 can utilize different techniques and layers or stacks of protocols, including, for example, the Ethernet protocol, the internet protocol suite (TCP/IP), the ATM (Asynchronous Transfer Mode) technique, the SONET (Synchronous Optical Networking) protocol, the SDH (Synchronous Digital Hierarchy) protocol, etc. The TCP/IP internet protocol suite can include application layer, transport layer, internet layer (including, e.g., IPv6), or the link layer. Network 101 can be a type of a broadcast network, a telecommunications network, a data communication network, a computer network, a Bluetooth network, or other types of wired and wireless networks.

Grounded virtual portal (GVP) system 100 can include any combination of hardware and software for providing a grounded virtual portal functionality to a user to perform medical procedures from a remote workspace 118 to a patient in a medical environment 180, via a network 101. computing system 130 can include an electronic component or a combination of an electronic component and a software component that delivers content to be rendered through the HMD 120. computing system 130 can manage network communication, user sessions, provide applications 154 for users to use, manage user profiles and provide security (e.g., via security module 142). computing system 130 can handle the data (e.g., video streams, event streams or kinematics streams) and provide tele transition controller and ground reference handler functionality. computing system 130 can include a network interface, ground reference handler, tele-transition controller and extended reality environment functions that can work together to determine a view of the extended reality 126 to be displayed at the HMD 120. computing system 130 can be provided on a cloud (e.g., as a software as service) or provided on a server 104. computing system 130 can be combined with (e.g., within) the HMD 120 to form a single device. In some implementations, computing system 130 is provided by any one or more (e.g., any combination of) the console 102 or server 104.

Computing system 130 can include the functionality to communicate with and provide services for the medical environment 180. computing system 130 can include a network interface 132 designed, constructed and operational to communicate with one or more components of system 100 via network 101, including, for example, the robotic medical system 186, HMD 120 or input controllers 112 (e.g., sensors 114 and/or actuators 116). Network interface 132 can include an electronic component or a combination of an electronic component and a software component that communicates with the system. Network interface 132 may communicate with a communication interface of the system through a communication link. The communication link may be a wireless link, a wired link, or both. Examples of the wireless link can include a cellular communication link, a near field communication link, Wi-Fi, Bluetooth, or any communication wireless communication link. Examples of the wired link can include a universal serial bus (USB), Ethernet, Firewire, high-definition multimedia interface (HDMI), or any wired communication link. Network interface 132 may communicate with the system via at least a bus connection or a conductive trace in examples where the system and the HMD are integrated on a single system. Network interface 132 may exchange data indicating the determined location of the HMD, the orientation of the HMD, and/or the user's gaze direction via the communication link or exchange data indicating the image to be rendered from the system via the communication link.

Device interface 134 can include any type and form of interface for one or more devices or systems. Device interface 134 can include an interface for a user to access or utilize a surgical platform in which a user can utilize input controllers 112 and HMD 120 to perform surgeries in a remote medical environments 180. Device interface 134 can include virtual representation of workspace 118 in which the user can utilize computer inputs (e.g., keyboards, computer mice or touch screens) to implement the functionalities of the control environments 110 and HMD 120.

Multiplayer Sync 136 can include any combination of hardware and software for allowing or coordinating two or more users (e.g., surgeons) to utilize the same robotic medical system 186 and share one or more medical tools 182. Multiplayer Sync 136 can be implemented into a robotic medical system that allows for coordination and collaboration between two or more medical professionals to collaborate on a medical procedure, such as a surgery. Multiplayer sync 136 can coordinate the use of medical tools 182 by one user as opposed to the other. Multiplayer sync 136 can allocate some medical tools 182 to a first user, while the other user can utilize other medical tools 182. For example, robotic medical system 186 can provide multiple arms for multiple users and the multiplayer sync 136 can coordinate the use and sharing of resources of the medical environment 180 by two or more users utilizing two or more workspaces 118 via the computing system 130.

In an illustrative example, multiple users can access an extended reality environment (e.g., a virtual reality) using respective HMDs and input controllers. A computing system 130 or server can host the virtual reality environment accessed by the multiple users. In the virtual reality environment, a first user using a first input controller can exert a force on a virtual object in the virtual reality environment. Exerting a force on a virtual object can be referred to or include a virtual force. The computing system 130 (or server) can identify the virtual force exerted on the virtual object (e.g., a virtual medical tool) by the first use, and activate an actuator of an input controller of a second user to exert a force via the input controllers in accordance with the identified virtual force, thereby conveying the force feedback to a second user.

Session manager 138 can include any combination of hardware and software for establishing and maintaining user sessions between one or more users (e.g., using HMDs 120) and the GVP 130. Session manager 138 can include the functionality for establishing connections and utilizing profile managers 140 of various users to provide the users with their corresponding settings and applications 154. Session manager 138 can utilize security module 142 to provide and implement user's authentication and authorization to allow the user to access the user's profile at the computing system 130.

Profile manager 140 can include any functionality for using and storing profiles of various users accessing and using computing system 130. For example, profile manager 140 can include and store user profiles. User profiles can include settings and access parameters for a user. User profiles can include or identify applications 154 that the user can access as well as user preferences and user history. Profile manager 140 can include and manage specific settings for user's access and operation of features related to the medical environments 180 and utilization of control environments 110.

Security module 142 can include any combination of hardware and software for controlling and providing network security and access control for the users of the computing system 130. Security module 142 can include user authentication features (e.g., username and password functionalities) as well as user access features. For example, security module 142 can include and provide access control for various users, based on their levels of access.

Hand tracker 144 can include any combination of hardware and software that uses data from various sensors 114 to monitor and analyze the movements of users' hands. Hand tracker 144 can include or utilize computer vision techniques (e.g., ML model 106) to use images or videos of user's hands to detect or discern various gestures that the user makes. Hand tracker 144 can operate in real time and allow the user to seamlessly interact with computing system 130. For instance, the user can use the hand tracker 144 to (e.g. via sensors 114 in the control environment 110) to control medical tools 182 in the medical environment 180. Hand tracker 144 can detect gestures, such as finger movements for scrolling or selecting items, hand waving for navigation or moving of objects, pinching or expanding fingers for zooming in or out, and making specific hand movements or shapes to trigger specific commands or actions.

Eye tracker 146 can include any combination of hardware and software for measuring, detecting, monitors and analyzing a user's gaze, including eye movements and locations. Eye tracker 146 can include the functionality to use the user's gaze (e.g., movements and locations of the eyes) to determine various user commands or actions, such as selections of features displayed. Eye tracker 146 can utilize sensor data (e.g., camera images) or infrared sensors to track the user's eye movements in real-time, allowing for accurate detection of where the user is looking with respect to the features displayed in the extended reality 126 on the display 122. Eye tracker 146 can interpret the user's visual focus and trigger actions such as selecting options, navigating through menus, activating controls, or even initiating specific commands without the need for physical input devices.

Playback controller 148 can include any functionality for playing audiovisual data for the user. Playback controller 148 can include a video player and/or audio player. Playback controller 148 can insert a portion of a video live feed into a part of an extended reality 126 displayed for the user via the HMD 120. Playback controller 148 can include the functionality for streaming video streams 162, event streams 164 or kinematic streams 166. Playback controller 148 can use the multi-channel file format to playback a medical procedure such that the user can feel the medical procedure. The playback controller 148 can playback the medical procedure with force feedback that is hi-fidelity or low-fidelity. For example, depending on the computing system 130 configuration and input controller 112 functionality or quality, the playback controller 148 can playback the medical procedure with hi-fidelity force feedback or low-fidelity force feedback. In some cases, the computing system 130 can playback the medical procedure in hi-fidelity or low-fidelity based on the type of procedure, or application (e.g., intraoperative, simulation, training, sales, or medical case review). In some cases, the computing system 130 can select the fidelity with which to playback the force feedback based on a profile of the user, available network bandwidth, computing resource capacity, load balancing, or level of subscription of the user.

Ground reference handler 150 can include any combination of hardware and software for determining and establishing a reference point 151, also referred to as a grounded reference frame 151, for a computing system 130. Ground reference handler 150 can include the functionality for determining a location that can be used as a reference point 151. The reference point or a frame of reference (e.g., grounded reference frame 151) can include any location in physical reality (e.g., a physical medical environment 180) or in a virtual or augmented reality. Grounded reference handler 150 can include the functionality for rendering image frames for the extended reality 126 displayed on the display 122 in accordance with the reference point or the frame of reference.

Grounded reference handler 150 can include a frame of reference or a reference point in a physical reality, such as a location in a medical environment 180. For example, a reference point can be a point or location within a medical environment 180 (e.g., surgical operating table, a location on a surgical bed, a location on a patient's body, or a location inside of an operating room). For example, a reference point can be a point or location within a control environment, such as a location or point in an office in which the user utilizes the input controllers 112 for controlling or implementing the operation, via a network 101, on a patient in a physical and remote medical environment 180.

Grounded reference handler 150 can include a frame of reference or a reference point in a virtual or augmented reality. For example, a reference point can be a point or location within a virtual representation (e.g., digital twin) of a medical environment 180 (e.g., virtual representation of a surgical operating table, a location on a virtual surgical bed, a location on a virtual patient's body, or a location inside of a virtual operating room). For example, a reference point can be a point or location within a virtual representation (e.g., digital twin) of a control environment 110, such as a location or point of the input controllers 112 that can be illustrated or rendered as a part of a virtual representation of a medical environment 180. For example, a reference point can be a point of the user's HMD 120, such as a virtual point between the user's eyes in the XR representation of the user in the virtual space. For example, a reference point can be a point of a particular sensor 114 or actuator 116 used for controlling the remote operation or providing data for rendering or providing the virtual representation of the extended reality 126 via the display 122 of the HMD 120.

Grounded reference frame 151 can include any fixed coordinate system or point of reference that remains stable and provides a basis for positioning and movement tracking of other components within a system 100. The grounded reference frame 151 can be any stable reference point or coordinate system used to define the positions and orientations of objects in space. The grounded reference frame 151 can include a set of coordinates fixed to, or in reference to, the base structure 185 of a system 100. In doing so, the grounded frame reference 151 can maintain all movements and positions to be measured relative to the same reference or point. For instance, in a surgical robotic medical system 186, the grounded reference frame 151 can be established based on the position of the base structure 185, allowing the input controller 112 and medical tools 182 to operate with precise spatial awareness. For example, in virtual reality environments, the grounded reference frame 151 can be used to rendering and interacting with virtual objects such that the virtual objects correspond correctly to the physical objects 187 in the user's physical space (e.g., the medical environment 180).

Extended reality environment 158 can include any combination of hardware and software for providing an extended reality 126 to be displayed to the user via the HMD 120. Extended reality environment 158 can include any combination of physical, actual, virtual or augmented reality based on or in accordance with the physical medical environment 180. Extended reality environment 158 can include or provide a virtual representation of the medical environment 180. Extended reality environment 158 can include or provide a virtual representation of a control environment 110. For example, extended reality can include or provide a virtual representation (e.g., a digital twin) of a medical environment 180 using real-time sensor 114 data provided via a video stream 162 along with the virtual representation of the input controllers (e.g., actuators 116 that the user controls to operate the medical tools 182). Extended reality environment 158 can receive feedback information (e.g., sensor data) from the medical environment 180 and/or input controllers 112 to keep track of the locations and movements of the user in the physical environment (e.g., medical environment 180) and in the virtual representation of the medical environment 180 that can be rebuilt as an extended reality 126 to be displayed to the user via the HMD 120.

Tele-transition controller 152 can include any combination of hardware and software for controlling or providing ability to switch between various points of views or realities provided to the user. Tele-transition controller 152 can include the functionality to allow the user to adjust a level of immersion in the extended reality environment. Tele-transition controller 152 can include the functionality to switch between different aspects of tele-navigation, such as for example viewing from a particular camera sensor 114 in a particular medical tool 182 to a particular view of a camera sensor on a wall of a medical environment 180. Tele-transition controller 152 can allow the user to switch (e.g., tele-manipulate the view) from the point of view of a virtual reality view in which several virtual features (e.g., patient's virtually rendered bones or internal organs) can be displayed and physical reality view in which the user can see the user's body as is (e.g., without the bones or organs exposed). Tele-transition can allow the user to tele-manipulate the computing system 130 so as to allow the user to use an application 154 for training a surgery or an application for analyzing the surgery after the fact.

The tele-transition controller 152 can dynamically switch between AR and VR based on the surgical system context and scene understanding-switching to mixed reality mode or directional dimming based on where the object or robotic arm is entering the scene, allowing a user to be aware of context and switch to VR mode. The tele-transition controller 152 can, therefore, facilitate use cases such as bedside assist wearing the HMD. The tele-transition controller 152 can dynamically control dimming or allow see through mode of arm or action detected in a volume where AR content is placed, or provide a virtual 3D monitor where a screen is placed.

In implementations, the tele-transition controller 152 can control the level of immersion in an extended reality environment. The tele-transition controller 152 can control the level of immersion based on user input or based on real-time operating room characteristics. In some cases, the tele-transition controller 152 can switch between augment reality and virtual reality modes based on cues from the system noting stage and activity of surgery (e.g., tasks or phases of the medical procedure) or interactions with other people or objects in the operating room. For example, the tele-transition controller 152 can enter a pass-through or see-through mode upon detecting the end of a medical procedure, an event or trigger condition in an event stream, or the presence of another person or object within a field of view of the user.

The tele-transition controller 152 can determine, identify, or predict a context of a surgical task or phase based user input. A user can provide input via an input controller 112, or the tele-transition controller 152 can receive input via the eye tracker 146 that can indicate a desired level of immersion. In some cases, the tele-transition controller 152 can predict the desired level of immersion based on inputting data captured for the medical procedure (including, e.g., event stream, kinematics stream, video stream, eye tracking data, or hand tracking data) into a machine learning model trained and configured to predict a task, phase, or desired level of immersion. The tele-transition controller 152 can understand context of surgical task or phase based on dialing in level of immersion, and automatically transition to an endoscopic view or a full operating room (e.g., medical environment 180) theater view based on adjusting the level of immersion of the extended reality environment.

Thus, the tele-transition controller 152 can facilitate one or more of tele-manipulation, tele-mobility, or tele-navigation. Tele-manipulation can refer to or include commanding or controlling a medical tool 182. The tele-transition controller 152 can determine when a user intends to transition to a telemobility task through, for example, motion, acceleration or physical position within a workspace 118 and adapt the tuning and properties of the input interface (e.g., input controller 112) or extended reality 126 to support effective movement in this task.

In tele-mobility, the system 130 can facilitate control of navigation of the body in 3D immersive spaces from the grounded controllers 112 of the system 130. The system 130 can allow or facilitate movement of a user within a virtual environment (e.g., extended reality environment 158) while the user is seated in at a console. The system can facilitate telemobility with telepresence by using controller 112 inputs to navigate the movement of the user from a physically seated position to a moving virtual experience in 3D space within the extended reality environment 158. While doing so, the system 130 can maintain hand-eye orientation during the experience as a result of the grounded reference frame established for the grounded HMD and grounded input controllers 112. The system 130 can provide tele-mobility features such as gliding or arc hopping through an extended reality environment based on input received from input controllers 112, hand tracker 144, or eye tracker 146, for example.

The system 130 can provide for tele-navigation, which can include one or more component or function of tele-navigation. Inputs for tele-navigation can be similar to inputs for telemobility, but the inputs can navigate a medical tool 182 or object such as a catheter or endoscope, as opposed to the user themselves in an extended reality environment 158. To perform tele-navigation of medical tools 182 or objects, the system 130 can utilize the scaling function 156 to provide various types of scaling, workspace centering using ratcheting, or medical tool recentering. For example, the system 130 can provide commanded endoscope recentering on a workspace, or re-scaling based on instrument extents or previously commanded zoom scale. The system 130 can transition in the extended reality 126 view between viewpoints during a live case observation, such as by going from an endoscope focused view to a operating room view, and while adjusting the scaling and recentering functionality accordingly.

Applications 154 can include any type and form of applications that a user can utilize via the workspace 118. Application 154 can include an application for analyzing a particular medial procedure (e.g., surgery or treatment) using video recordings of an actual surgery performed. Application 154 can include an application for training on a virtual surgery using virtual reality. Application 154 can include an application for a user to collaborate with one or more other surgeons to perform parts of a surgery, allowing a first user to implement some of the tasks, while other user(s) perform other tasks.

Applications 154 can include configuration settings for user interface elements, profiles, scaling functions, force scaler functions, or constraints for a particular application or use case, such as full peri-operative use cases, learning, preoperative, intraoperative, or postoperative. Applications 154 can provide various features or functionality, such as an feature for marking anatomy via the computing system 130 using the eye tracker 146 and hand tracker 144 to track gestures. The computing system 130 can provide for remote proctor placing a virtual anatomical marker by eye gauge and input controller or hand gesture. A computing system 130 application 154 can include hybrid surgery based on eye-tracking. A computing system 130 application 154 can include collaborative surgery with a surgical assist to provide retraction or camera control assistance, for example.

Scaling function 156 can include any combination of hardware and software for scaling the movements or control in a virtual reality version of a workspace 118. For example, a scaling function 156 can include a functionality for determining that a virtual representation of a surgical opening is only a first distance long (e.g., 1 cm) in the extended reality 126 displayed on the HMD 120. The scaling functionality 156 can also include the functionality for determining (e.g., via sensors 114 data received from the medical environment 180) that the actual surgical opening in the physical medical environment 180 is ten times larger than the first distance (e.g., 10 cm). The scaling function 156 can determine that the virtual representation of the workspace in the extended reality allows for scaling of the surgery opening view by a factor of 5 or 10 times. In response to this, the scaling function 156 can zoom in and increase the size of the surgical opening for the user in accordance with the allowable scaling and the limits to the virtual representation of the workspace.

The system 130 can identify user intent for dynamic scaling, such as for coarse controls or fine controls, which can facilitate performance when working in smaller workspaces (e.g., workspace 118 of the computing system 130) relative to a larger medical environment 180 (e.g., an operating room in which the robotic medical system 186 can be located). motion scaling; optimizing camera motion for smaller space; re-centering to where surgeon is working.

The system 130 can use one or more types of scaling functions 156, or select a scaling function 156 from a plurality of scaling functions 156 stored in memory. The system 130 can set, adjust, or otherwise configure a scaling function 156 based on understanding a context associated with a medical task, phase or activity. Examples of scaling functions the system 130 can use include: kinematic scaling, visual field scaling, fidelity scale invariant scaling, ballistics, dynamic scaling, background re-centering, or workspace ratcheting.

Kinematic scaling can refer to or include a scaling function with a scale factor. For example, the scale factor from the input controller 112 of the computing system 130 to the medical tool 182 of the robotic medical system 186 can be a ratio of 1 to 2, 1 to 3, 1 to 3, 1 to 4, 1 to 6, 1 to 8 or greater, for example. Thus, a unit of movement of the input controller 112 detected by the hand tracker 144 (or a sensor 114 of the input controller 112) can correspond to multiple units of movement in the medical tool 182 of the robotic medical system 186.

The computing system 130 can perform visual field scaling in which the scaling between the extended reality 126 presented via the display 122. The visual field scaling can refer to displaying an amount of volume in the extended reality 126 that corresponds to a volume in the medical environment 180 or a volume perceived by the robotic medical system 186. using visual field scaling, the computing system 130 can reduce the amount of volume via cropping, zooming, or both. The computing system 130 can determine to perform visual field scaling based on the context associated with the task, activity or phase of the medical procedure.

In an illustrative example, the input controller 112 workspace 118 can be approximately 8 times smaller than the workspace available to the robotic medical system 186. For example, the robotic medical system 186 can include input controllers that may have a 1:1 scaling to the medical tool 182 at the patient side, whereas the input controllers 112 of the computing system 130 can have a scaling of 8:1 to the input controller of the robotic medical system 186. Thus, to traverse the same visual field in the external reality 126 as would be seen with the robotic medical system 186, the kinematic scaling for the GVP would be 8:1 instead of 1:1. This also can result in movement that is 8 times as fast, which could impact performance of the medial procedure, efficiency, or duration. In some cases, the computing system 130 can construct the visual volume of the extended reality 126 to be 8 times smaller than the visual volume of the robotic medical system 186, thereby retain the 1:1 kinematic scaling. In some cases, the computing system 130 can select intermediate scaling (e.g., 2:1 or 4:1). In some cases, the computing system 130 can use a combined scaling function in which a user can change a scaling option, and the computing system 130 can intelligently and automatically compensate kinematic and visual scaling to render an experience that is comparable to the full-size console experience provided by the robotic medical system 186 in the smaller computing system 130 form factor.

The computing system 130 can provide motion scaling without sacrificing motion fidelity in order to improve the user experience and training translation in a smaller GVP form factor. To do so, the computing system 130 can be configured with or provide for fidelity scale invariant motion scaling to facilitate translating from a relatively small interface (e.g., the computing system 130 with HMD 120 and input controller 112) to a larger input controller form factor (e.g., robotic medical system), and can support a clinical working volume in the medical environment from a physically small computing system 130 workspace.

To provide fidelity scale invariance, the computing system 130 can have an anti-tremor function that can include utilizing a spatial filter, so that motion in the computing system 130 is mapped to scaled and spatially smooth motion in simulation or at the robotic medical system side. The system 130 can employ a continuum between spatial filtering with light scaling for dissection tasks and gesture recognition at the extreme of high scaling (e.g., bowel raking in a GVP). This can refer to or include motion automation on the input side, which can allow the computing system 130 to provide scale invariance.

Figure 14A:
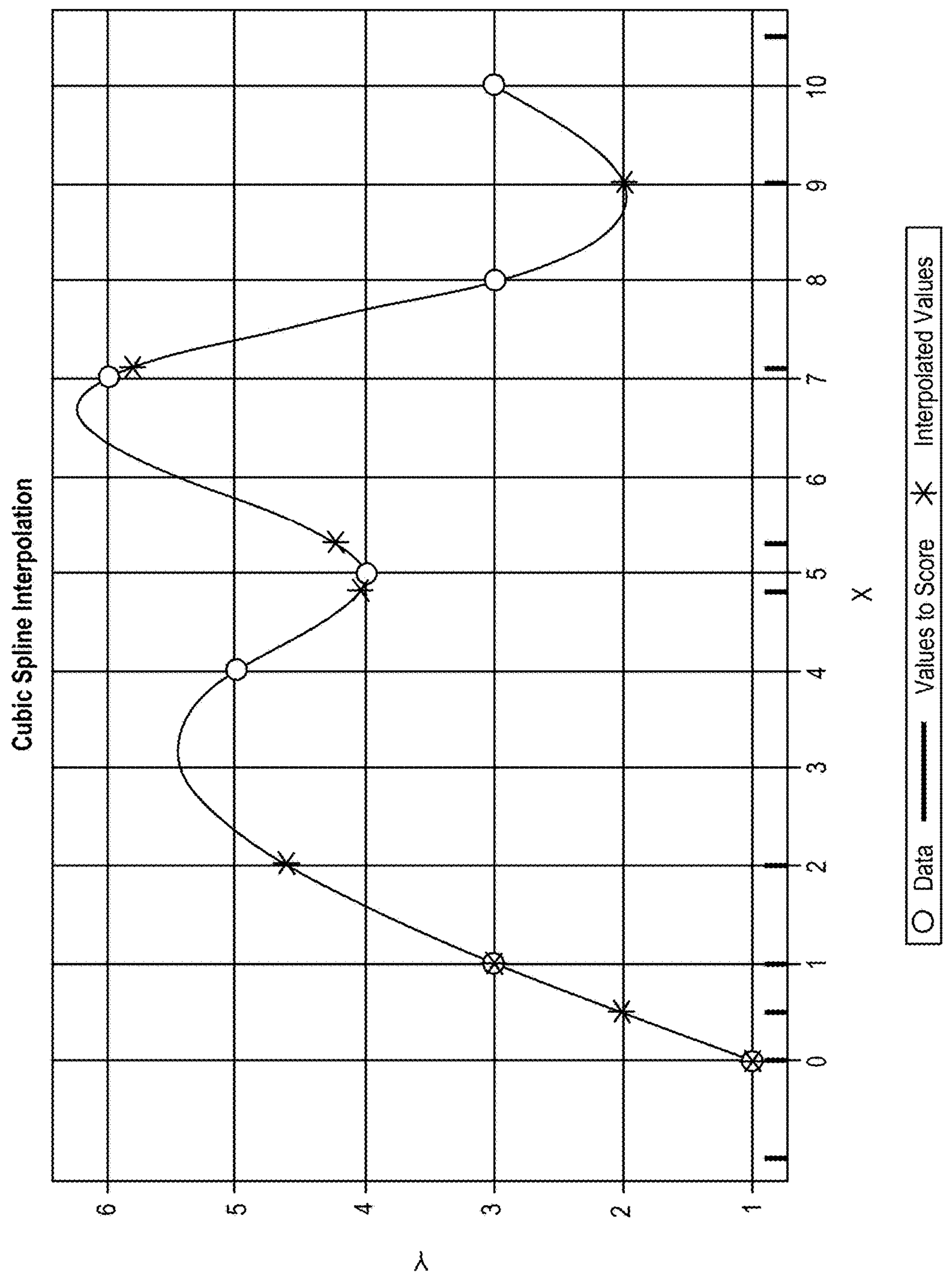
FIGS. 14A-14B depict example transfer functions for scaling, in accordance with embodiments.

In some cases, the computing system 130 can utilize motion scaling with anti-tremor temporal filter, which in the smaller workspace can apply scaling to both intended motion but also unwanted motion noise artifacts. In terms of actual fidelity scale invariance implementation, the motion trajectory can be a real time spline curve fit of GVP commanded position (e.g., depicted in FIG. 14A). Scale invariance can result when a point density in the spline (e.g., depicted as example 1400 in FIG. 14A) scales with the scale factor between the controller and robotic system or simulation side so that the point density is a nominal value in robot/simulation space, and independent of scale factor. The computing system 130 can implement fidelity scale invariance for use cases such as tele-training, as it can preserve control fidelity independent of scale, and allow for a small training workspace to translate to a larger working volume.

Figure 14B:
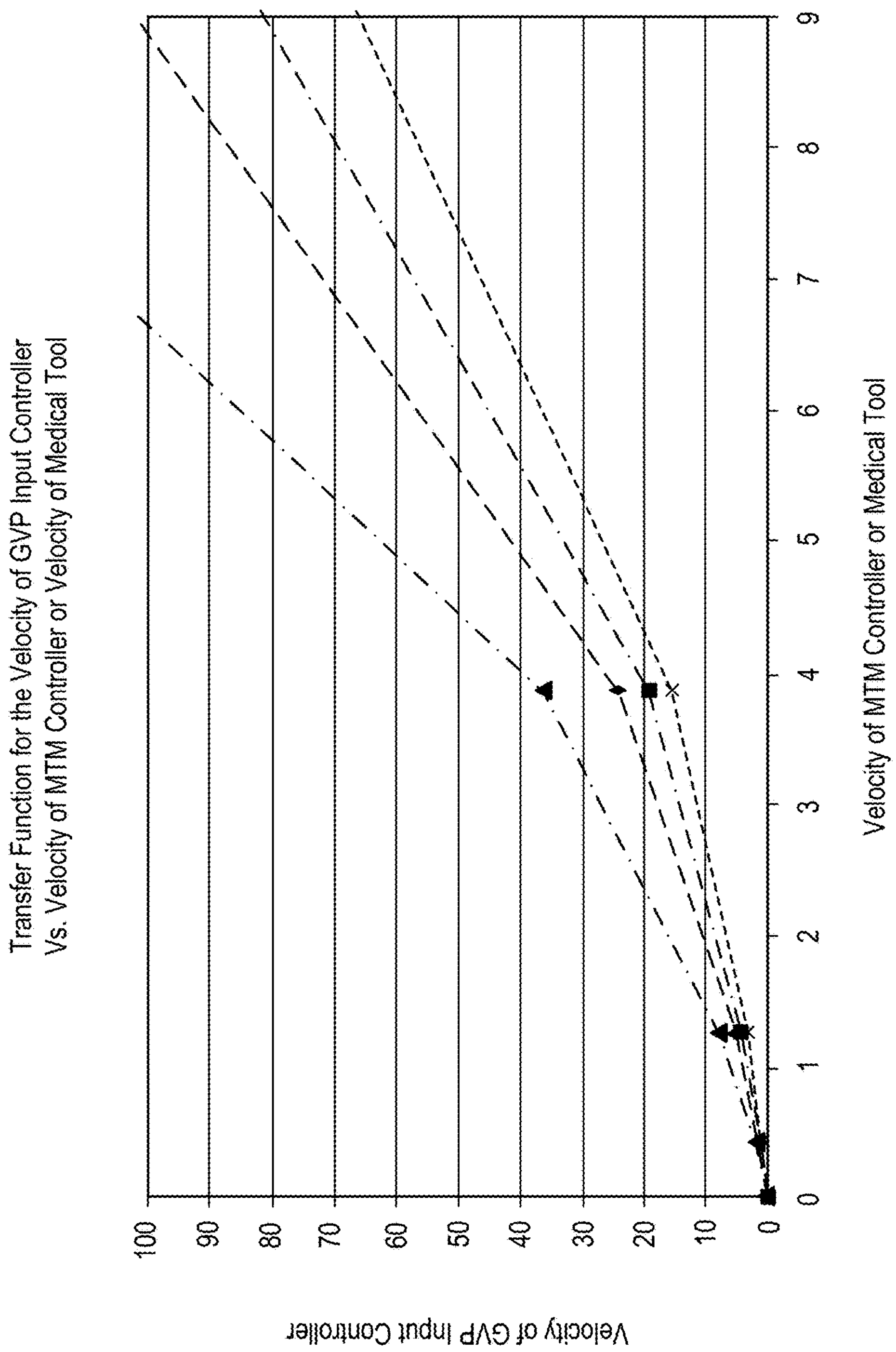

The computing system 130 can be configured with a ballistics based scaling function or technique. In some cases, the computing system 130 can account for user preference by changes to the order of the curve fit as well as incorporation of ballistics. Ballistics can refer to or include a technique in which rendered velocity is a function of commanded velocity (e.g., as depicted by the transfer function illustrated as example 1450 in FIG. 14B). The computing system 130 can utilize ballistics so that precise motion is provided at low velocity, but at large velocity (e.g., for bowel raking), the working volume can be effectively larger. The computing system 130 can implement or utilize ballistics for intraoperative use cases, but may disable ballistics for training uses where the console may not implement ballistics.

The computing system 130 can be configured with or perform dynamic scaling. Using dynamic scaling, the computing system 130 can allow for a small workspace to be effectively similar to a larger workspace. For example, UI metrics such as frequency of clutching, average working volume and frequency of excursions near the limits of the workspace may allow for a slow shift in scale factor that supports the functional working volume. This shift in scale factor can be slow enough and continuous so that commanded motions are faithfully captured and rendered. The computing system 130 can provide dynamic scaling as a user option for the intraoperative use case, while disabling dynamic scaling from the training use case.

The computing system 130 can provide for background re-centering (or motion ratcheting), which can refer to or include a non-linear mapping where commanded motion towards the edges of the workspace 118 have a smaller gain in translation to robotic system frame in medical environment 180 than motions towards the center of the workspace 118. Motion towards the center can be a continuous background process that minimizes the amount of position clutching that would be used in a smaller console workspace. The difference in directional displacement gain may be a few percent towards or away from the center of the workspace, which may not be noticeable to the user, but the computing system 130 can use background re-centering to keep the user centered on the workspace, which is beneficial for the GVP that has a small working volume. Background re-centering can provide ergonomic advantages as well and allow a user clutch to their preferred spot in the GVP workspace 118. The computing system 130 can use background re-centering for the intraoperative use case.

Data handler 160 can include any combination of hardware and software for receiving and handling data for the computing system 130. Data handler 160 can include the functionality for capturing, receiving or obtaining data from one or more component or system associated with the medical environment 180 or control environment 110, via the network 101. Data handler 160 can include the functionality for processing the data, including generating video stream 162 (e.g., from images and videos from camera sensors 114), event streams 164 or kinetics streams 166. Data handler 160 can receive and/or generate environment characteristics and force feedback stream. Data handler 160 can receive and/or generate ML feature stream 172.

Video stream 162 can include any collection or stream of video data or images. For example, a captured medical process (e.g., surgery) can be provided for viewing from one or more cameras (e.g., data capture devices 184 or medical tools 182) which can be compiled or included in a video stream 162. Video stream 162 can include a series of image frames from various angles or vintage points in relation to the procedure activity (e.g., point or area of surgery), as well as any sound data, temperature data, pressure data, patient's vital signs data, or any other data corresponding to the procedure). One or more consecutive frames of video data may be included in video stream 162, from any number of vintage points. Video stream 162 can include extended reality video (e.g., rendered video) that can use one or more combined physical video data along with one or more virtual features.

Event stream 164 can include a stream of event data or information, such as packets, that identify or convey a state of the robotic medical system 186 or an event that occurred in association with the robotic medical system 186 or surgical or medical surgery being performed with the robotic medical system. Events indicated in the event stream 164 can include installation dates of tools, dates or timestamps of procedural actions, or data involving patients or users. Data of the event stream 164 can be captured by the robotic medical system 186 or a data capture device 184. For example, robotic medical system 186 can indicate whether the medical tool 182 is installed on a manipulator arm of the robotic medical system, whether it was calibrated, or whether it was fully functional (e.g., without errors) during the procedure. For example, when the medical tool 182 is installed on a manipulator arm of the robotic medical system 186, a signal or data packet(s) can be generated indicating that the medical tool has been installed on the manipulator arm of the robotic medical system 186. Another example state of the robotic medical system 186 can indicate whether the visualization tool 124 is connected, whether directly to the robotic medical system or indirectly through another auxiliary system that is connected to the robotic medical system.

Kinematics stream 166 can include any information or data describing motion or position of objects in a system (e.g., physical or virtual representation of it). Kinematics stream 166 can include a continuous flow of data indicating the motion and position of medical tools 182 in a medical environment 180. Kinematics stream 166 can include a continuous flow of data indicating a virtual location of a virtual representation of a medical tool 182 based on the control of the input controllers 112 (e.g., actuators 116) by a user in a workspace 118. Kinematic stream 166 can include data including parameters, such as, position, orientation, velocity, acceleration, and angular velocity of objects (e.g., medical tools) or body parts (e.g., relative position of the HMD 120 of the user). Kinematic stream 166 can include data that is timestamped in order to be synchronized with the video stream 162 and event stream 164.

Environment stream 168 can include any data of an environment. Environment stream 168 can include a stream of temperature data, pressure data or humidity data. Environment stream 168 can include patient's vital signs data or any health related information (e.g., heart rate, body temperature or medical device readings). Environment stream 168 can include time stamped data for allowing synchronization with other data streams.

Force feedback stream 170 can include data indicating force or strength of movement. Force feedback stream 170 can include data indicative of magnitude of force of movement, such as amount of force to apply or push in a particular direction with a particular medical tool 182. Force feedback stream 170 can include data providing a push back information, such as information indicative of how hard is patient's body pushing against the medical tool 182 (e.g., in terms of Newtons of force). Force feedback stream 170 can include time stamped data to allow for synchronization with other data streams.

ML feature stream 172 can include any stream of data from a ML model 106. ML feature stream 172 can include data or information including predictions as to the tasks or actions performed by a user in a particular operation or surgery. ML feature stream 172 can include predicted or determined spatial dependencies or relationships with respect to video stream 162 input into the model. ML feature stream 172 can include a data stream indicative of detected actions or parts of procedure performed, based on the streamed data or locations of particular medical tools 182 within the patient's body and with respect to patient's internal organs, based on the stream data.

Computing system 130 can include one or more force scalers 174, also referred to as force scaler functions 174, generating, applying or using one or more force parameters 176 to provide, generate and/or apply force as a feedback to the user via the input controllers 112. Force scaler 174, or a force scaler function 174, can include any combination of hardware and software for generating, controlling and/or applying force towards or against input controllers 112 to indicate to the user that the medical tools 182 handled by the user (e.g., whether physical or virtual version of the tools) experiences at the operation (e.g., surgery) site. Force scaler 174 can include a function that utilizes data from the force feedback stream 170 to generate, produce or provide force, or a representation of force or resistance that the user can feel with the hands or any other part of the body the user may use to operate any functionality of the system 100.

Force scaler 174 can include the functionality for generating or applying a mechanical force, vibration, haptic feedback to convey the sensation of force, pushback, pressure, tension, friction, compression, strain, stiffness or resistance being felt by the medical tool 182 at the site of the operation (e.g., medical environment 180). Force scaler 174 can generate or apply force feedback to the input controllers of the user, simulating the sensations that the medical tools 182, whether physical or a virtual representation of the tool, experiences or would experience during a medical operation, such as surgery. In AR or VR applications or representations, force scaler 174 can simulate the force, pushback or resistance that the surgeon would feel at the site and provide (e.g., via haptic feedback, vibration, tension, strain, stiffness, resistance or any other feedback) indication to the user that the force, pushback or resistance is being experienced. Force scaler 174 can provide or cause haptic feedback, replicating the tactile sensations and resistance that a surgeon is encountering (e.g., in a physical environment) or would encounter (e.g., in a virtual environment) while manipulating surgical instruments via the system 100. For instance, when using a virtual representation of a scalpel during a simulated surgery, the force scaler 174 can apply varying levels of resistance, stiffness, pressure or haptic feedback to the user's input controllers 112, mimicking the feeling of cutting through tissues. The intensity of the feedback or sensation can increase commensurate with the resistance, pushback, stiffness, friction, tension or force felt. Force parameters 176 can be used by the force scaler 174 to define or indicate the intensity of the force to be provided or generated. Similarly, in the case of a physical robotic medical system, the force scaler 174 can generate force feedback (e.g., using the force parameters 176) to convey the pressure exerted by the instruments against the patient's tissues during the actual surgical procedure. Force scalar function can take into account different aspects of a kinematics chain that can include one or linkages, degrees of freedom, inertia, force, tension, or elasticity. The force scalar function can provide active force or have passive force.

Force parameters 176 can include any one or more values indicating the intensity and/or direction of the force, pushback, pressure, tension, friction, compression, strain, stiffness or resistance. Force parameters 176 can be determined and generated by the force scaler 174 responsive to the data from sensors 114 or actuators 116 at the medical environment 180 or any other part of the system 100. Force parameters 176 can include a vector data indicating direction of the force and the magnitude of the force. Force parameters 176 can include a vector or array of values indicating the force intensity and direction that is felt or experienced by the medical tools 182 over a period of time (e.g., force changing through time). Force parameters 176 can be used by the force scaler 174 to control or manage actuators 116 on the input controllers 112 to apply the determined or generated force, resistance or pushback in a manner that causes the user to feel the sensation via the input controllers 112.

Computing system 130 can include one or more constraint controllers 178 with one or more constraint parameters 180. Constraint controller 178 can include any combination of hardware and software to determine and apply constraints to physical range of movement of the input controllers in accordance with the actual constraints at the site of the operation. Constraint controller 178 can determine and apply constraints to the range of motion of any number of linked structural components holding or supporting the input controllers 112, thereby providing or generating a sensation that the user can feel as a limitation to the range of motion of the medical tools 182 (whether physical or virtual) at the surgery site. Constraint controller 178 can work together with the force controller 174 to provide a final stop or a limit to the freedom of movement after the force controller 174 has already indicated (e.g., via feedback on the input controllers) to the user that a resistance or pushback has been felt.

Constraint controller 178 can include the functionality to assess the limitations or restrictions in the freedom of movement for remotely controlled medical tools 182 (or their virtual counterparts) at a physical or virtual surgery location. Constraint controller 178 can generate constraint parameters 180 for any number of linked components (e.g., linkage components) to generate a total available range of motion at the input controller 112 held in place (e.g., grounded) via the linkage components. Linkage components can be added, removed, or swapped out. The swappable physical linkages can include or have constraints which can be taken into account by the computing system 130. Constraint controller 178 can determine or define the constraint limitations to the structural linkage components holding the input controllers 112 via constraint parameters 180, which can include or define the physical boundaries and restrictions encountered during the remote surgery (e.g., whether physical or virtual). For example, if a robotic medical system 186 detects a structural limit in the articulation of its endoscopic tool, the constraint controller 178 can generate a constraint parameter 179, also referred to as a constraint 179, or a constraint value 179, that can be used by the actuators 116 at the input controllers 112 to limit the range of motion along a direction of an input controller 112. Constraint controller 178 can use breaks or movement limiting mechanisms (e.g., controlled encoder motors, clutches, friction brakes) to limit the movement of the linked components holding the input controllers 112.

Constraint parameters 179 (e.g., constraints 179 or constraint values 179) can include any values or parameters to limit or curtail a range of movement. Constraint parameters 179 can be used to indicate the range of movement which the constraint controller 178 can use to cause the limited range of motion for the input controllers 112. Constraint parameters 179 can include values that can indicate coordinates with respect to a particular location (e.g., length, width and height coordinate values) which can define a volumetric (e.g., 3D) space for the freedom of movement. Constraint parameter 179 can include a vector indicating a barrier or a limit to the movement and a direction with respect to the movement being barred. Constraint parameters 179 can include values or parameters for each individual linkage, or each physical structural movable component, between the ground or desk at which the base of the input controllers 112 assembly to the input controllers 112 that the user is handling.

Console 102 can include any combination of hardware and software for providing a user interface or control panel with a centralized and interactive platform for accessing, managing, and controlling features or functionalities of a computing system 130. Console 102 can include a computing system 300 and provide any feature or functionality of a computing system 130, workspace 118 and/or medical environment 180. Console 102 can be locally deployed at the workspace 118 or a medical environment 180. Console 102 can wirelessly communicate with the HMD 120 and exchange data and controls. Console 102 can act as an intermediary device for providing communication between HMD 120 of a user and medical environment 180. Consoles 102 can include, for example, personal surgeon console (e.g., to practice cases, telementoring, virtual content and collaboration), sales console (e.g., a mobile console, support presentations, demonstrate experience, remote case observations), a resident console (e.g., exposure and training via the robotic medical system), or an employee console (e.g., for training, visual operating room, viewing live surgery, product development, or virtual collaborations). The console 102 can include the HMD and input controllers. Console 102 can include a computing device.

Server 104 can include any type and form of a network device communicating over a network 101. Server 104 can include a computing system 300 and can be used to provide computing system 130. Server 104 can include or correspond to a server farm or a virtual server of a virtual private network or a cloud-based service. Server 104 can store access, provide and share data, can facilitate functionality of the GVP 130, any feature of workspace 118 and medical environment 180. Server 104 can include and provide one or more ML models 106.

ML model 106 can include any machine learning model that can provide any data of a ML feature stream 172. ML model 106 can include a model performing a temporal and/or spatial feature extraction of information or data from a stream (e.g., a video stream, event stream or kinematics stream). ML model 106 can include or correspond to a model trained using attention-based deep learning. ML model 106 can use the multi-pathway spatial-temporal decoding unit based on the attention-based deep learning model (e.g., first model) to generate moment-to-moment predictions of phase. ML model 106 can include a multi-pathway spatial-temporal decoding unit comprising an attention-based deep learning model. ML model 106 can be based on or leverage a vision transformer architecture with self-attention over space and time to provide jointed spatial and temporal feature learning from the videos.

ML model 106 can be trained with machine learning based on historical workflows (e.g., historical data from prior video streams 162, event streams 164 or kinematics streams 166). ML model 106 can include a long-range temporal module trained, configured or otherwise generated based on an analysis of surgical workflows to model a distribution over phases at each moment in time that serves as a prior belief. ML model 106 can be configured with or incorporate information about logical workflows to augment the information gained from another (e.g., vision-based model determining actions from video data). ML model 106 can combine information about both the average duration of phases and the temporal ordering of phases, so that at each timestep the data processing system 130 can define, identify or otherwise establish a prior belief of the likelihood of staying within the same phase, or transitioning to each of the other phases of an operation.

Thus, the computing system 130 can provide for bidirectional control and feedback with physical or virtual objects in an XR environment. In doing so, the computing system 130 can use scaling functions, force scaler factors, and grounded reference frames that are established, configured, tuned, or calibrated for an HMD 120, input controller 112, or workspace 118. The computing system 130 can scale video and motion dependent on a particular reference frame, level of immersion in an XR environment, types of linkages or other parameters.

In an example, a technical solution can include a GVP system 100 a ground reference frame 151 (e.g., a reference point) and one or more linkages 181 can be used to configure a force delivery between an input controller 112 and an object 187 of a medical environment 180. For instance, a system 100 can include an input controller 112 that can include any number of sensors 114 and actuators 116. The input controller 112 can be coupled, via one or more (e.g., a plurality of) linkages 181, to a first structure 183. The first structure 183 can be mechanically coupled to a base structure 185. The input controller 112 can be configured to control an object of a medical environment 180. The system 100 can include a head mounted display 120 coupled to a second structure 183 that extends from the base structure 185. The head mounted display 120 can be configured to render an extended reality environment 158 corresponding to the medical environment 180, such as an extended reality 126 representation of the medical environment 180. The system 100 can include one or more processors 310 that can be coupled with memory 315 or 320 storing instructions or data that configures the one or more processors 310 to implement acts of a computing system 130. For instance, once executed, the instructions and data stored in memory 315 can configure the one or more processors 310 to establish a grounded reference frame for the input controller to be maintained in the extended reality environment (e.g., 126) rendered via the head mounted display 120. For instance, once executed, the instructions and data stored in memory 315 can configure the one or more processors 310 to configure, based on the plurality of linkages 181 and the grounded reference frame 151, a force scaler function (e.g., 174) for bidirectional force delivery between the input controller 112 and the object of the medical environment 180.

One or more linkages 181 of the plurality of linkages 181 can include, or operate according to, one or more (e.g., a plurality of) degrees of freedom. The one or more processors 310 can be configured (e.g., based on the instructions stored in memory 315 or 320) to apply a constraint 179 to the linkage 181 to limit an amount of movement in a degree of freedom. For instance, the one or more processors 310 can limit a degree of freedom of a linkage 181 to a particular range of motion, such as a range of degrees from a central axis of the linkage 181.

The one or more processors 310 can be configured to select the constraint 179 based on a type of the linkage 181. The type of the linkage can include or correspond to at least one of a boom-mount, a cart-mount, or a floor-mount system. For example, the constraint controller 178 can select the constraint 179 based on a dimension of a workspace comprising the input controller. For example, the one or more processors 310 can implement the constraint controller 178 to select the constraint 179 based on a dimension of the medical environment 180 in the extended reality environment 158. The one or more processors 310 can be configured to select the constraint 179 in accordance with a degree of freedom of a medical tool of a robotic medical system 186 in the medical environment 180.

The one or more processors 310 can be configured to select the force scaler function 174, based on a type of medical procedure performed in the medical environment 180. The one or more processors 310 can be configured to select the force scaler function 174 based on at least one of a task, a phase, or an activity performed in the medical environment 180. The one or more processors 310 can be configured to select the force scaler function 174 based on a profile of a user engaged with the head mounted display 120. The one or more processors 310 can be configured to select the force scaler function 174 based on a profile of a user engaged with the head mounted display 120.

The one or more processors 310 can be configured to the force scaler function 174 comprises a spatial filter configured to map interactions with the input controller to spatially smooth motion of the object 187. The one or more processors 310 can be configured to detect a transition in a level of immersion of the extended reality environment 158. The one or more processors 310 can be configured to adjust, responsive to the detection of the transition in the level of immersion of the extended reality environment 158, a parameter 176 of the force scaler function 174.

The one or more processors 310 can be configured to detect a change in at least one of a task, activity or phase associated with a procedure performed in the medical environment 180. The one or more processors 310 can be configured to transition, responsive to the detection of the change, a level of immersion of the extended reality environment 158. The one or more processors 310 can be configured to adjust, responsive to the transition in the level of immersion of the extended reality environment 158, a parameter 176 of the force scaler function 174.

The one or more processors 310 can be configured to detect a transition in a level of immersion of the extended reality environment 158. The one or more processors 310 can be configured to apply a constraint 179 to an amount of movement in one or more degrees of freedom of at least one of the input controller or a linkage 181 of the plurality of linkages 181. The one or more processors 310 can be configured to detect a change in at least one linkage 181 of the plurality of linkages 181. The one or more processors 310 can be configured to adjust the force scaler function 174 responsive to the detection in the change in the at least one linkage 181. The one or more processors 310 can be configured to detect an addition to, or removal from, the plurality of linkages 181. The one or more processors 310 can be configured to adjust the force scaler function responsive to the detection in the addition or the removal. The head mounted display 120 can be mechanically coupled to the first structure 183, and the object can be a medical tool 182 of a robotic medical system 186 located in the medical environment 180. The object 187 can be a virtual object, and the medical environment 180 can be a virtual reality environment (158), such as for example a medical environment 180 depicted in an extended reality environment 158.

The system can include one or more cameras (114), coupled to the head mounted display 120 and orientated, directed to, coupled with or turned towards the input controller 112. The one or more processors 310 can be configured to receive data captured from the one or more cameras (e.g., 114) and determine interactions with the input controller 112 based on the data captured from the one or more cameras (e.g., 114). The one or more processors 310 can be configured to receive a visual data feed captured by the one or more cameras (e.g., 114) and apply a hand tracking function (e.g., hand tracker 144) to the visual data feed to detect the interactions with the input controller 112. The one or more processors 310 can be configured to generate, based on the interactions detected via application of the hand tracking function (144), an instruction to control at least one of manipulation or movement of the object 187.

The one or more processors 310 can be configured to receive multi-channel data feed of a medical procedure performed in the medical environment 180 via a physical robotic medical system 186 comprising the object 187. The object 187 can include a physical medical tool 182. The one or more processors 310 can be configured to generate, from the multi-channel data feed, the extended reality environment 158 comprising a virtual robotic medical system corresponding to the physical robotic medical system 186 and a virtual medical tool corresponding to the physical medical tool 182. The one or more processors 310 can be configured to generate, from the multi-channel data feed, a force feedback stream 170. The one or more processors 310 can be configured to play a video stream 162 of the multi-channel data feed via the extended reality environment 158 rendered by the head mounted display 120. The one or more processors 310 can be configured to control an actuator 116 of the input controller 112 in accordance with the force feedback stream 170 translated based on the force scaler function 174, and in synchronization with the video stream played by the head mounted display. The multi-channel data feed comprises can include the video stream 162, an event stream 164 recorded by the physical robotic medical system 186, environment characteristics 168 associated with the medical procedure performed via the physical robotic medical system 186, and a kinematics stream 166 captured by the physical robotic medical system 186.

Figure 2A:
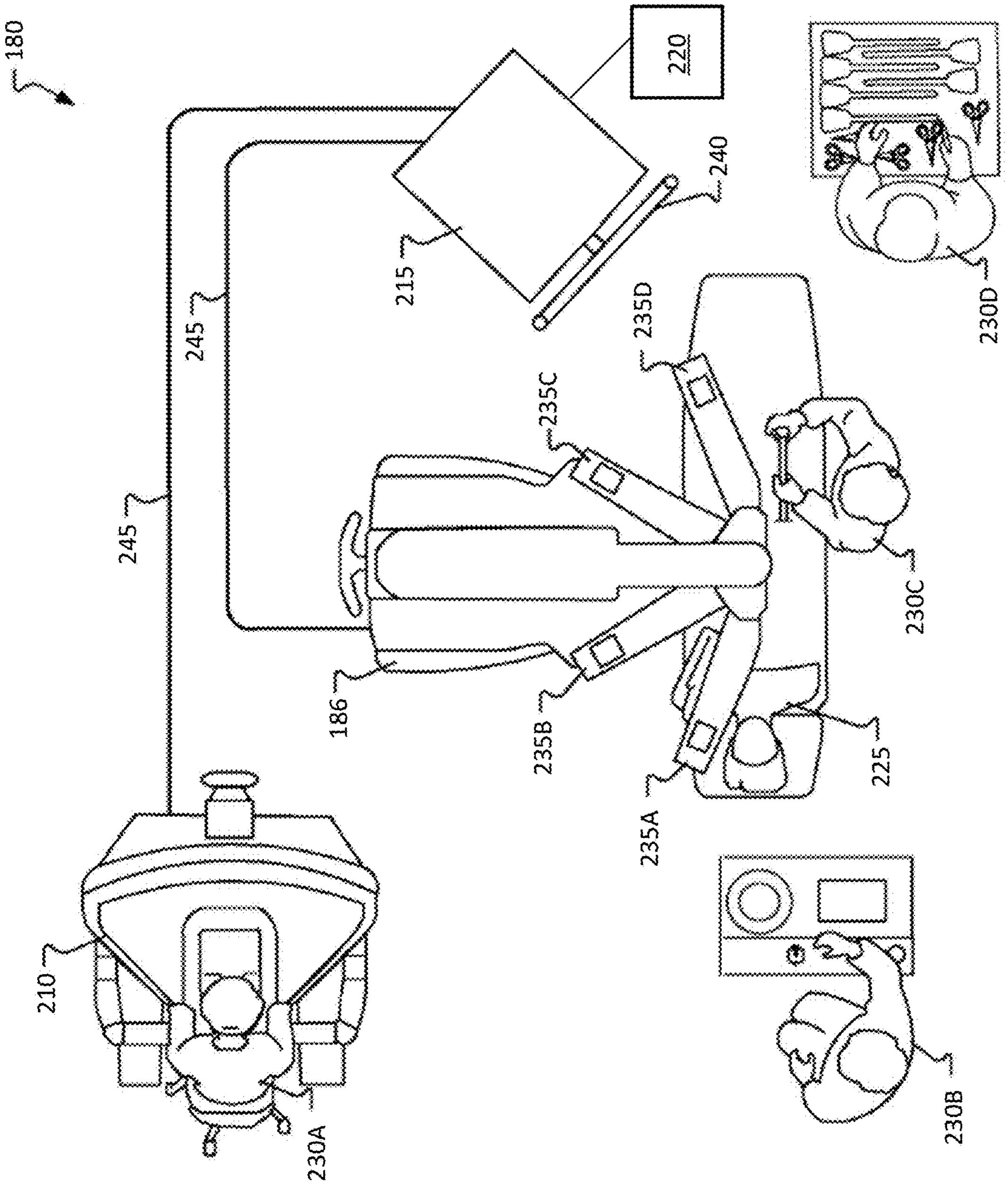
FIG. 2A depicts an example medical environment, in accordance with embodiments of the present solution.

The one or more processors 310 can be configured to select, based on a mode, a level of fidelity with which to play the force feedback stream 170. The mode can be one of intraoperative, case review, training, or sales. The one or more processors 310 can be configured to actuate the input controller 112 in accordance with the selected level of fidelity. FIG. 2A depicts an example medical environment 180, in accordance with embodiments. The medical environment 180 can refer to or include a surgical environment or surgical system. The medical environment 180 can include a robotic medical system 186, a user control system 210, and an auxiliary system 215 communicatively coupled one to another. A visualization tool 220 (e.g., the visualization tool 124) can be connected to the auxiliary system 215, which in turn can be connected to the robotic medical system 186. Thus, when the visualization tool 220 is connected to the auxiliary system 215 and this auxiliary system is connected to the robotic medical system 186, the visualization tool can be considered connected to the robotic medical system. In some embodiments, the visualization tool 220 can additionally or alternatively be directly connected to the robotic medical system 186.

The medical environment 180 can be used to perform a computer-assisted medical procedure on a patient 225. In some embodiments, surgical team can include a surgeon 230A and additional medical personnel 230B-230D such as a medical assistant, nurse, and anesthesiologist, and other suitable team members who can assist with the surgical procedure or medical session. The medical session can include the surgical procedure being performed on the patient 225, as well as any pre-operative (e.g., which can include setup of the medical environment 180, including preparation of the patient 225 for the procedure), and post-operative (e.g., which can include clean up or post care of the patient), or other processes during the medical session. Although described in the context of a surgical procedure, the medical environment 180 can be implemented in a non-surgical procedure, or other types of medical procedures or diagnostics that can benefit from the accuracy and convenience of the surgical system.

The robotic medical system 186 can include a plurality of manipulator arms 235A-235D to which a plurality of medical tools (e.g., the medical tool 182) can be coupled or installed. Each medical tool can be any suitable surgical tool (e.g., a tool having tissue-interaction functions), imaging device (e.g., an endoscope, an ultrasound tool, etc.), sensing instrument (e.g., a force-sensing surgical instrument), diagnostic instrument, or other suitable instrument that can be used for a computer-assisted surgical procedure on the patient 225 (e.g., by being at least partially inserted into the patient and manipulated to perform a computer-assisted surgical procedure on the patient). Although the robotic medical system 186 is shown as including four manipulator arms (e.g., the manipulator arms 235A-235D), in other embodiments, the robotic medical system can include greater than or fewer than four manipulator arms. Further, not all manipulator arms can have a medical tool installed thereto at all times of the medical session. Moreover, in some embodiments, a medical tool installed on a manipulator arm can be replaced with another medical tool as suitable.

One or more of the manipulator arms 235A-235D or the medical tools attached to manipulator arms can include one or more displacement transducers, orientational sensors, positional sensors, or other types of sensors and devices to measure parameters or generate kinematics information. One or more components of the medical environment 180 can be configured to use the measured parameters or the kinematics information to track (e.g., determine poses of) or control the medical tools, as well as anything connected to the medical tools or the manipulator arms 235A-235D.

The user control system 210 can be used by the surgeon 230A to control (e.g., move) one or more of the manipulator arms 235A-235D or the medical tools connected to the manipulator arms. To facilitate control of the manipulator arms 235A-235D and track progression of the medical session, the user control system 210 can include a display (e.g., the display 122) that can provide the surgeon 230A with imagery (e.g., high-definition 3D imagery) of a surgical site associated with the patient 825 as captured by a medical tool (e.g., the medical tool 182, which can be an endoscope) installed to one of the manipulator arms 235A-235D. The user control system 210 can include a stereo viewer having two or more displays where stereoscopic images of a surgical site associated with the patient 225 and generated by a stereoscopic imaging system can be viewed by the surgeon 230A. In some embodiments, the user control system 210 can also receive images from the auxiliary system 215 and the visualization tool 220.

The surgeon 230A can use the imagery displayed by the user control system 210 to perform one or more procedures with one or more medical tools attached to the manipulator arms 235A-235D. To facilitate control of the manipulator arms 235A-235D or the medical tools installed thereto, the user control system 210 can include a set of controls. These controls can be manipulated by the surgeon 230A to control movement of the manipulator arms 235A-235D or the medical tools installed thereto. The controls can be configured to detect a wide variety of hand, wrist, and finger movements by the surgeon 230A to allow the surgeon to intuitively perform a procedure on the patient 225 using one or more medical tools installed to the manipulator arms 235A-235D.

The auxiliary system 215 can include one or more computing devices configured to perform processing operations within the medical environment 180. For example, the one or more computing devices can control or coordinate operations performed by various other components (e.g., the robotic medical system 186, the user control system 210) of the medical environment 180. A computing device included in the user control system 210 can transmit instructions to the robotic medical system 186 by way of the one or more computing devices of the auxiliary system 215. The auxiliary system 215 can receive and process image data representative of imagery captured by one or more imaging devices (e.g., medical tools) attached to the robotic medical system 186, as well as other data stream sources received from the visualization tool. For example, one or more image capture devices (e.g., the data capture devices 184) can be located within the medical environment 180. These image capture devices can capture images from various viewpoints within the medical environment 180. These images (e.g., video streams) can be transmitted to the visualization tool 220, which can then passthrough those images to the auxiliary system 215 as a single combined data stream. The auxiliary system 215 can then transmit the single video stream (including any data stream received from the medical tool(s) of the robotic medical system 186) to present on a display (e.g., the display 122) of the user control system 210.

In some embodiments, the auxiliary system 215 can be configured to present visual content (e.g., the single combined data stream) to other team members (e.g., the medical personnel 230B-230D) who may not have access to the user control system 210. Thus, the auxiliary system 215 can include a display 240 configured to display one or more user interfaces, such as images of the surgical site, information associated with the patient 225 or the surgical procedure, or any other visual content (e.g., the single combined data stream). In some embodiments, display 240 can be a touchscreen display or include other features to allow the medical personnel 230A-230D to interact with the auxiliary system 215.

The robotic medical system 186, the user control system 210, and the auxiliary system 215 can be communicatively coupled one to another in any suitable manner. For example, in some embodiments, the robotic medical system 186, the user control system 210, and the auxiliary system 215 can be communicatively coupled by way of control lines 245, which can represent any wired or wireless communication link as can serve a particular implementation. Thus, the robotic medical system 186, the user control system 210, and the auxiliary system 215 can each include one or more wired or wireless communication interfaces, such as one or more local area network interfaces, Wi-Fi network interfaces, cellular interfaces, etc.

It is to be understood that the medical environment 180 can include other or additional components or elements that can be needed or considered desirable to have for the medical session for which the surgical system is being used.

Figure 2B:
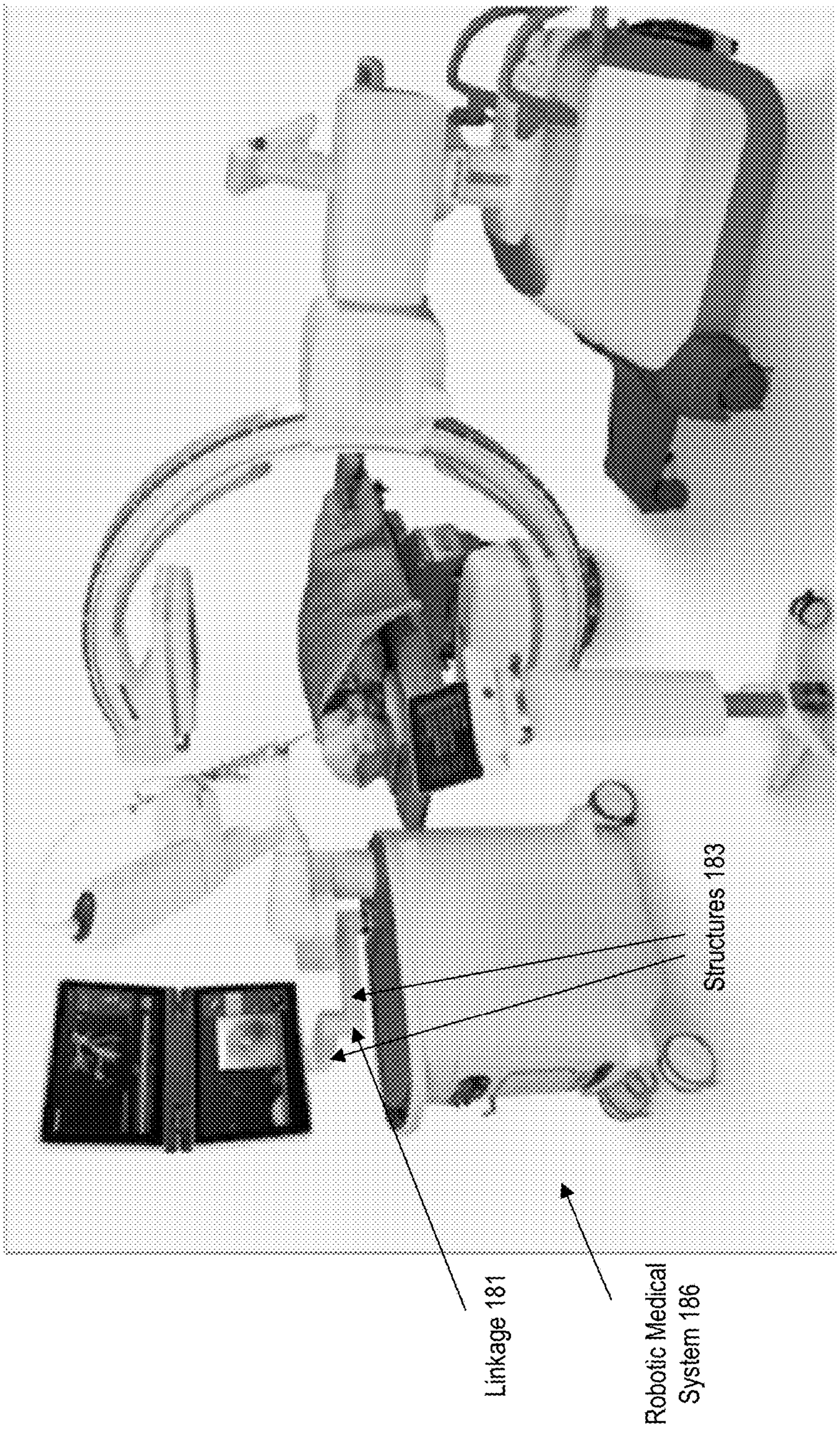
FIG. 2B depicts an example robotic-assisted platform for lung biopsy via a maneuverable catheter, in accordance with embodiments of the present solution.

FIG. 2B depicts an example 250 of a robotic-assisted platform for lung biopsy via a maneuverable catheter, in accordance with embodiments of the present solution. Example 250 of FIG. 2B can relate to a robotic-assisted platform for biopsies, such as a lung biopsy. Example 250 can include a medical environment 180 in which a robotic medical system 186 is mechanically coupled with, or includes, one or more structures 183 connected via one or more linkages 181. The example system can be used to obtain tissue samples from small nodules in the lung using a maneuverable catheter allowing the users to access and biopsy lesions across different parts of the lung.

Figure 3:
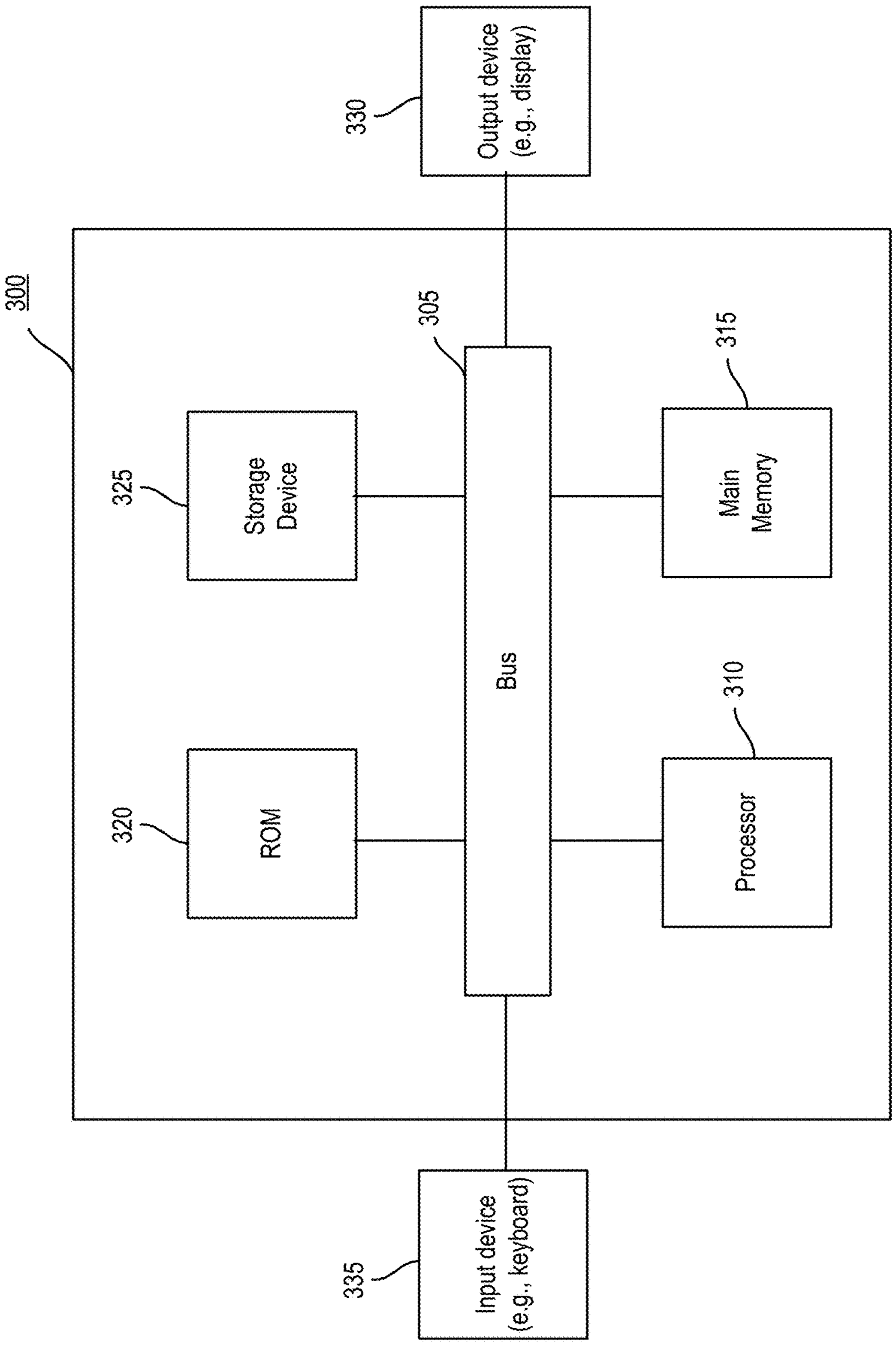
FIG. 3 is a block diagram depicting an architecture for a computer system that can be employed to implement elements of the systems and methods described and illustrated herein, in accordance with embodiments of the present solution.

FIG. 3 is a block diagram depicting an architecture for a computer system 300 or a computing environment 300 that can be employed to implement elements of the systems and methods described and illustrated herein. For example, the computing system 130, robotic medical system 186, console 102 or server 104 can each include one or more component or functionality of computing system 300. The computer system 300 can be any computing device used herein and can include or be used to implement a data processing system or its components. The computer system 300 includes at least one bus 305 or other communication component or interface for communicating information between various elements of the computer system. The computer system further includes at least one processor 310 or processing circuit coupled to the bus 305 for processing information. The computer system 300 also includes at least one main memory 315, such as a random-access memory (RAM) or other dynamic storage device, coupled to the bus 305 for storing information, and instructions to be executed by the processor 310. The main memory 315 can be used for storing information during execution of instructions by the processor 310. The computer system 300 can further include at least one read only memory (ROM) 320 or other static storage device coupled to the bus 305 for storing static information and instructions for the processor 310. A storage device 325, such as a solid-state device, magnetic disk or optical disk, can be coupled to the bus 305 to persistently store information and instructions.

The computer system 300 can be coupled via the bus 305 to a display 330, such as a liquid crystal display, or active-matrix display, for displaying information. An input device 335, such as a keyboard or voice interface can be coupled to the bus 305 for communicating information and commands to the processor 310. The input device 335 can include a touch screen display (e.g., the display 330). The input device 335 can also include a cursor control, such as a mouse, a trackball, or cursor direction keys, for communicating direction information and command selections to the processor 310 and for controlling cursor movement on the display 330.

The processes, systems and methods described herein can be implemented by the computer system 300 in response to the processor 310 executing an arrangement of instructions contained in the main memory 315. Such instructions can be read into the main memory 315 from another computer-readable medium, such as the storage device 325. Execution of the arrangement of instructions contained in the main memory 315 causes the computer system 300 to perform the illustrative processes described herein. One or more processors in a multi-processing arrangement can also be employed to execute the instructions contained in the main memory 315. Hard-wired circuitry can be used in place of or in combination with software instructions together with the systems and methods described herein. Systems and methods described herein are not limited to any specific combination of hardware circuitry and software.

The processor 310 can execute one or more instructions associated with the system 100. The processor 310 can include an electronic processor, an integrated circuit, or the like including one or more of digital logic, analog logic, digital sensors, analog sensors, communication buses, volatile memory, nonvolatile memory, and the like. The processor 310 can include, but is not limited to, at least one microcontroller unit (MCU), microprocessor unit (MPU), central processing unit (CPU), graphics processing unit (GPU), physics processing unit (PPU), embedded controller (EC), or the like. The processor 310 can include, or be associated with, a memory 315 operable to store or storing one or more non-transitory computer-readable instructions for operating components of the system 100 and operating components operably coupled to the processor 310. The one or more instructions can include at least one of firmware, software, hardware, operating systems, or embedded operating systems, for example. The processor 310 or the system 100 generally can include at least one communication bus controller to effect communication between the system processor and the other elements of the system 100.

The memory 315 can include one or more hardware memory devices to store binary data, digital data, or the like. The memory 315 can include one or more electrical components, electronic components, programmable electronic components, reprogrammable electronic components, integrated circuits, semiconductor devices, flip flops, arithmetic units, or the like. The memory 315 can include at least one of a non-volatile memory device, a solid-state memory device, a flash memory device, a NAND memory device, a volatile memory device, etc. The memory 315 can include one or more addressable memory regions disposed on one or more physical memory arrays.

Although an example computing system has been described in FIG. 3, the subject matter including the operations described in this specification can be implemented in other types of digital electronic circuitry, or in computer software, firmware, or hardware, including the structures disclosed in this specification and their structural equivalents, or in combinations of one or more of them.

Figure 4A:
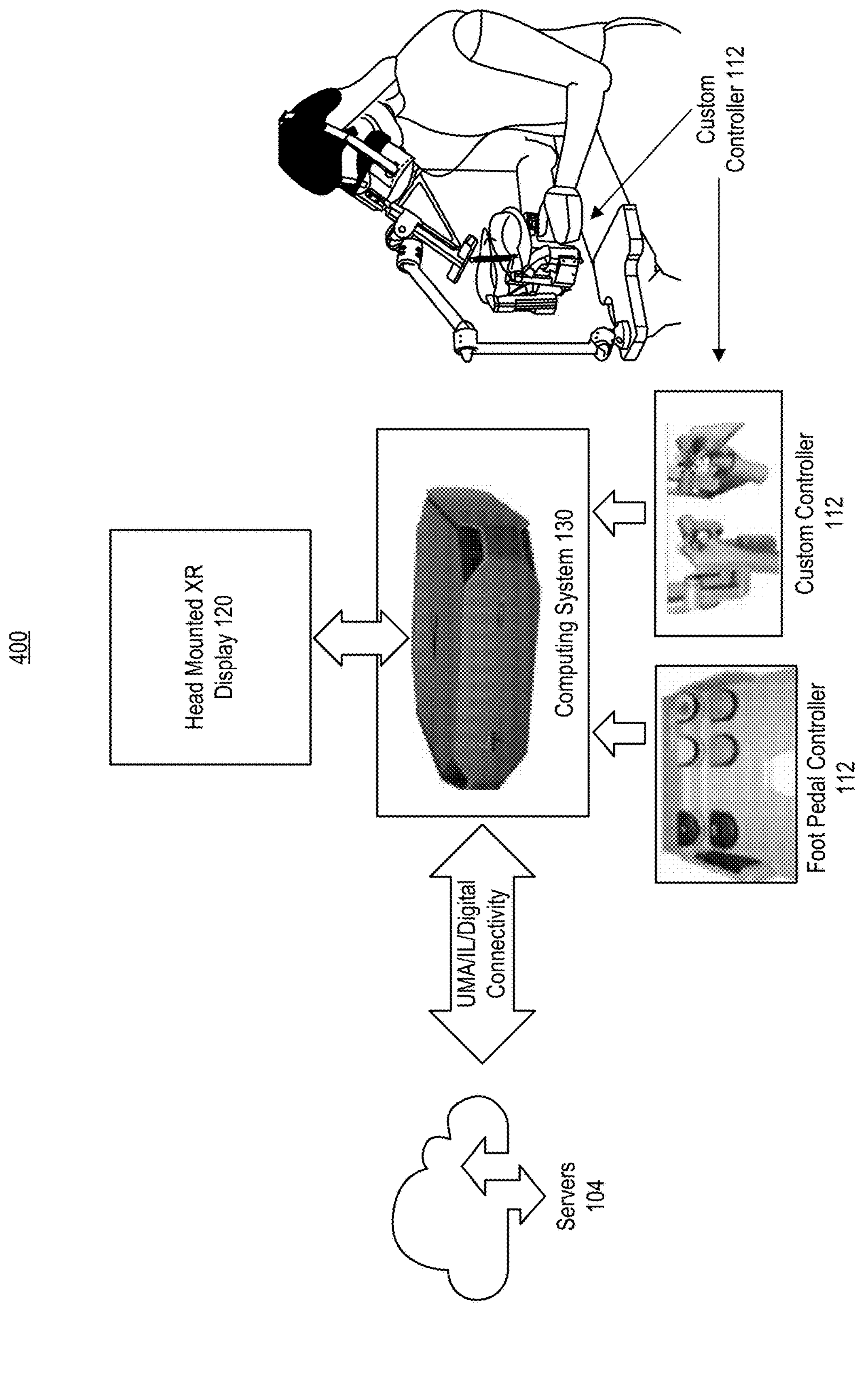
FIG. 4A depicts an example block diagram of a GVP system for allowing users to perform remote medical procedures.

FIG. 4A depicts an example block diagram 400 of a GVP system 100 for performing remote medical procedures. The GVP system 100 can include one or more component or functionality depicted in FIG. 4B, including, for example a computing system 130, HMD 120, or input controllers 112. The example computing system 130 of FIG. 4A can allow a user (e.g., a surgeon) to utilize actuators 116 of a control environment 110 to control virtually operated medical tools 182. In some cases, the computing system 130 can be implemented on a console 102. The example computing system 130 can include a VR display as an HMD 120, that the user can use for visual display of the extended reality 126 video frames. The computing system 130 can connect with the VR display (e.g., HMD 120) and act as a console 102 for the user. The computing system 130 can be communicatively coupled, via UMA/IL/Digital connectivity with one or more cloud applications (e.g., computing system 130 functionalities) provided by a software as a service (SaaS) on a cloud. The example GVP system 100 can include a control environment 110 of a workspace 118 and an HMD 120. The user can utilize the control environment 110 that can include a custom input controller 112 and Bluetooth (e.g., wirelessly coupled) foot pedals (e.g., foot pedal controller 112) for the user to use as actuators 116 to control a remotely operated set of medical tools 182 at a remote medical environment 180. Grounded HMD and input controllers can improve telepresence and precision. Grounded HMD and controllers can better align the user to the surgical task and allow for greater focus, which leads to a safe, effective, and more efficient surgery despite the surgeon not being collocated to the patient.

Figure 4B:
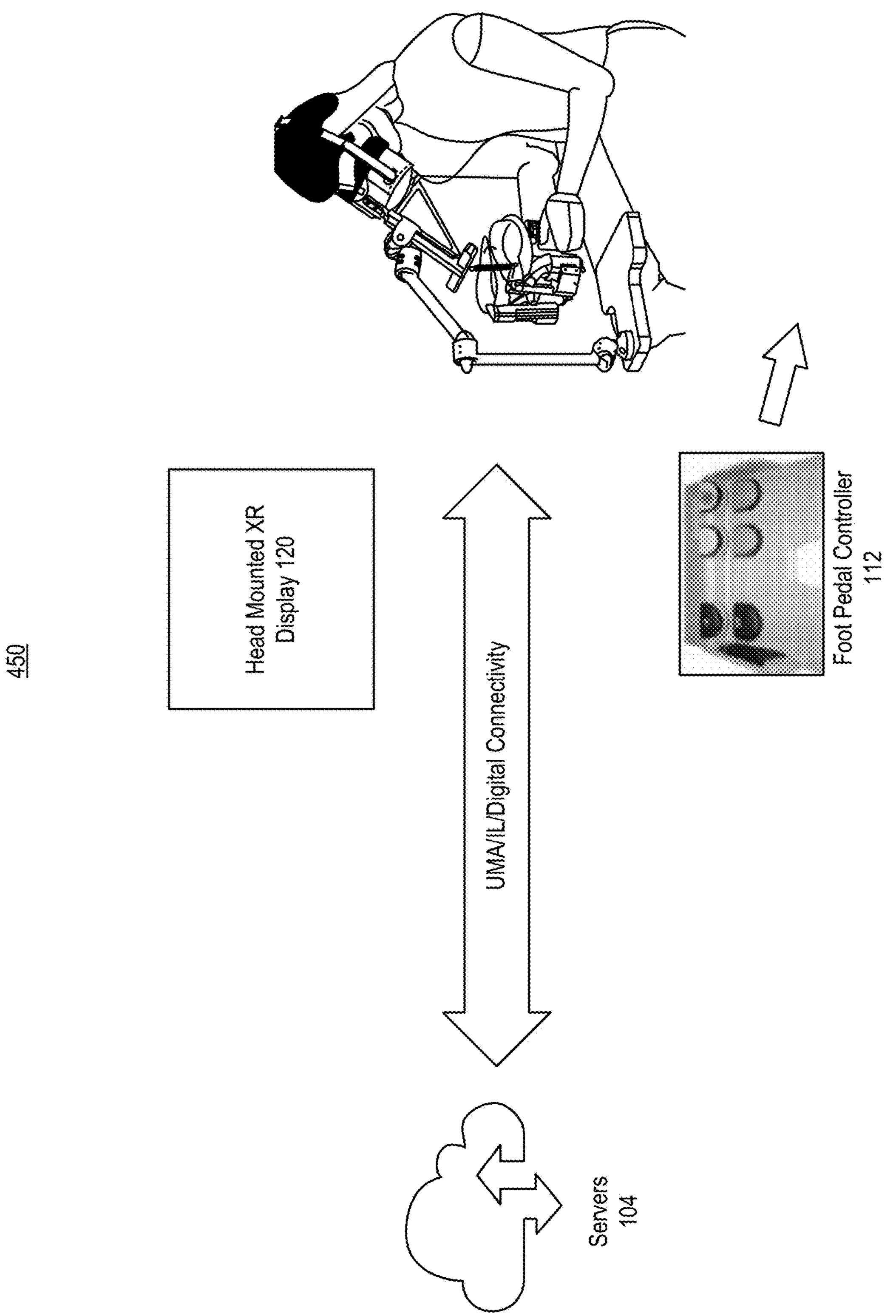
FIG. 4B depicts another example block diagram of a GVP for allowing users to perform remote medical procedures.

FIG. 4B depicts another example block diagram 450 of a GVP system 100 for performing remote medical procedures. In FIG. 4B, the components and functionality of computing system 130 depicted in FIG. 1 can be hosted on or provided by one or more servers 104. For example, servers 104 can include one or more component or functionality of computing system 130, in which case the HMD, input controllers 112, such as a foot pedal controller 112, can communicate with servers 104 via a network 101.

The servers 104 of FIG. 4B can allow a user (e.g., a surgeon) to utilize actuators 116 of a control environment 110 to control virtually operated medical tools 182 without the use of an intermediary console 102 disposed between the user at the control environment 110 and a remote cloud service. The head mounted XR display of FIG. 4B can include a VR display as an HMD 120, which the user can use for visual display of the extended reality 126 video frames. The features of the user's control environment 110 (e.g., actuators 116 and/or sensors 114) can be coupled with the cloud services (e.g., computing system 130). Control environment 110 can include, for example, a computing system 300 for providing the control environment 110 with accessibility for network communication with the cloud services via UMA/IL/digital connectivity. As with FIG. 4A, in FIG. 4B, the user can utilize the actuators 116 of control environment 110, including for example, a custom input controller and Bluetooth (e.g., wirelessly coupled) foot pedals for the user to use to control a remotely operated set of medical tools 182 at a remote medical environment 180.

Figure 5A:
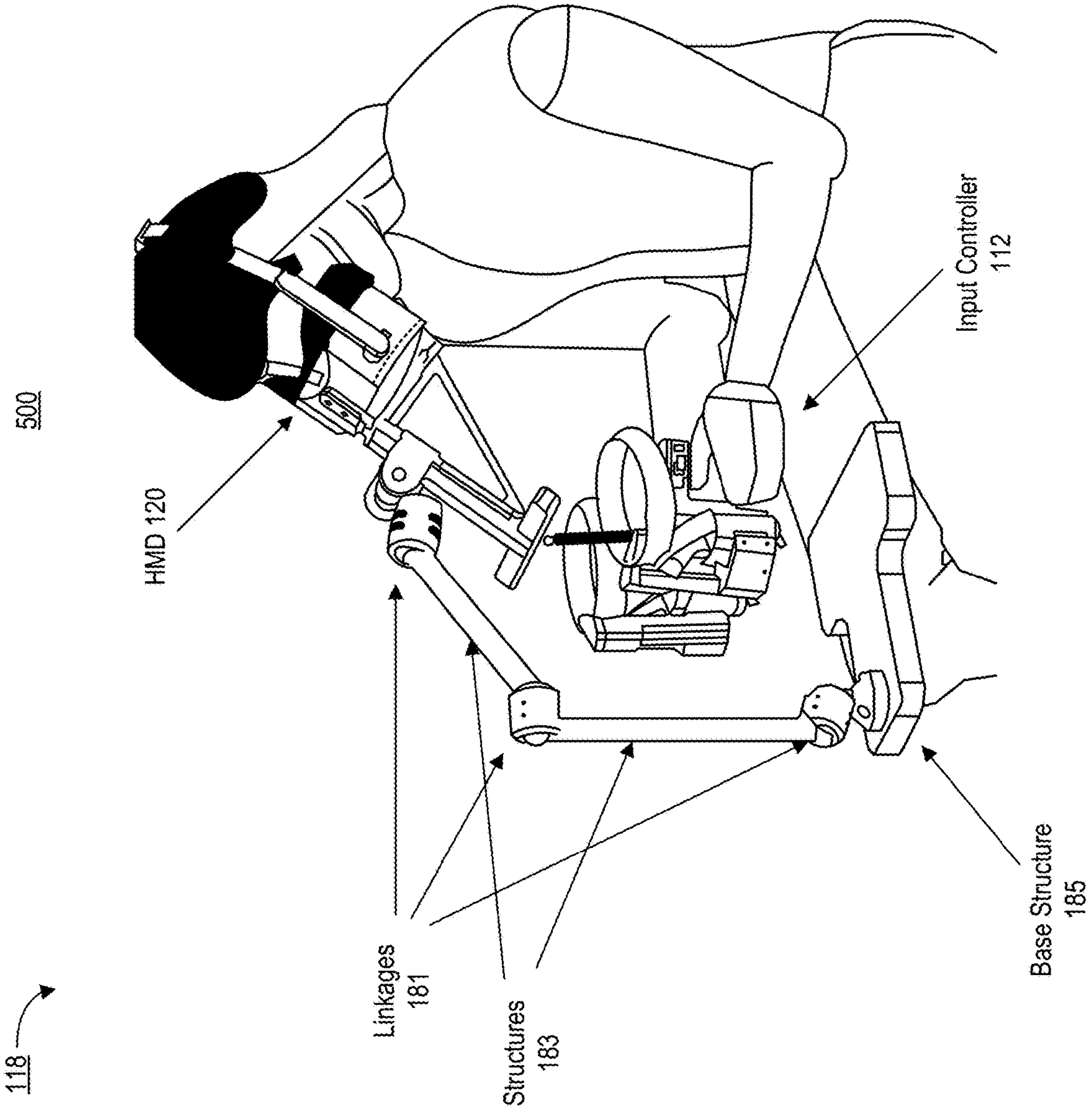
FIG. 5A-5C depict example consoles of a grounded virtual portal, in accordance with an embodiment of the present solution.

FIG. 5A depicts an example block diagram 500 of a workspace 118 of a grounded virtual portal, in accordance with an embodiment of the present solution. The workspace 118 can include HMD 120 to provide a visual feedback to the user in the form of video streams of extended reality 126, including the actual, augmented and virtual features. The control environment 110 can include one or more input controllers 112 that can include one or more sensors 114 and actuators 116 to allow the user to control remotely control medical tools 182, data capture devices 184 and/or robotic medical systems 186 across one or more medical environments 180.

Workspace 118 can include structures 183, such as mounts or support rods. Workspace 118 can include one or more linkages 181 that can be provided between the structures 183, all of which can be mounted on, or supported by, a base structure 185 (e.g., a 3D printed base), such as via a mounting bracket. The mounts or structures 183 and linkages 181 can support the HMD. The control environment 110 can include spring-loaded arms with 3D printed input controller grips and mounting bracket for the hand controllers (e.g., input controllers 112). The hand controllers can include one or more actuators 116 (e.g., buttons, levers and joysticks) as well as sensors 114 (e.g., pressure sensors, haptic sensors, force sensors, vibration sensors or any other type of sensor that can be used to provide feedback to the user). The mounting brackets or other support linkages can be configured to maintain Cartesian degrees of freedom. The input controllers 112 can include sensors 114 that can sense grip force, and actuators that can provide force feedback (e.g., inertia or vibration). The sensed grip force can be replicated through the instrument to provide user mediated haptics (e.g., sense use interaction and display or convey information about the interaction remotely). The input controllers 112 can be configured with touch points and provide modal control (e.g., clutch in and clutch out). Thus, the input controllers 112 can convey force interactions in a bi-directional manner or the net effect of force. With the bi-directional delivery of force information, the computing system 130 can provide an indication to user as to whether a tissue feels right or loose, for example.

The HMD depicted in FIG. 5A can be grounded (e.g., fixed, attached or otherwise coupled) to a support structure. The HMD depicted in FIG. 5A can be ungrounded or detached from the support structure. When detached or decoupled from the support structure, the GVP system 100 can detect that the HMD was detached and cause the tele-transition controller to take an action. The action can include adjusting an XR mode from AR to VR, a level of immersion, the type of information provided for display, scaling function, or force scaler function, for example.

Figure 5C:
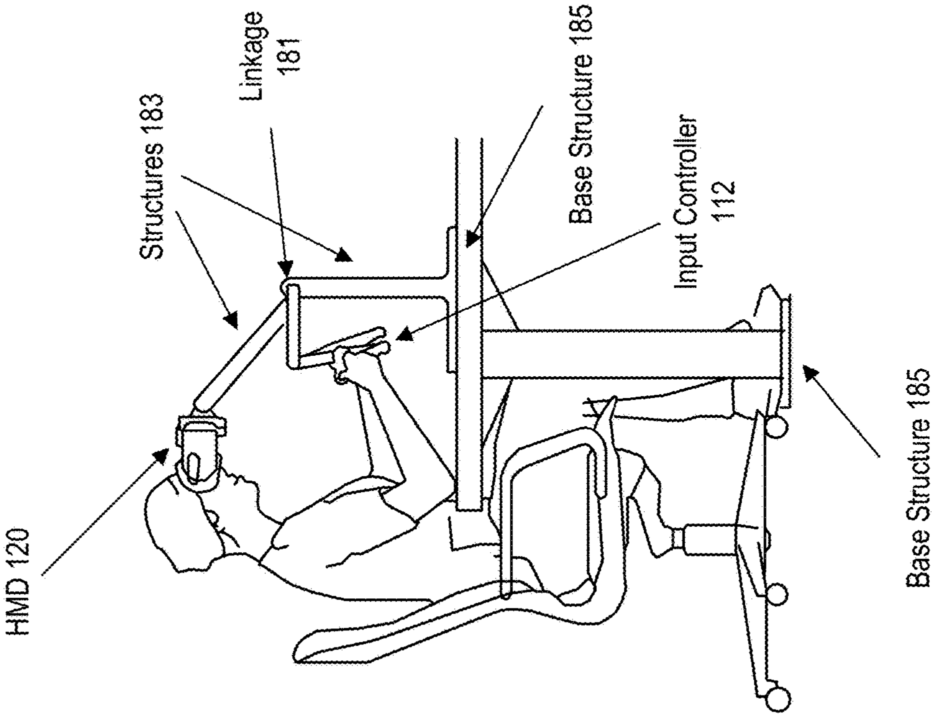
Figure 5B:
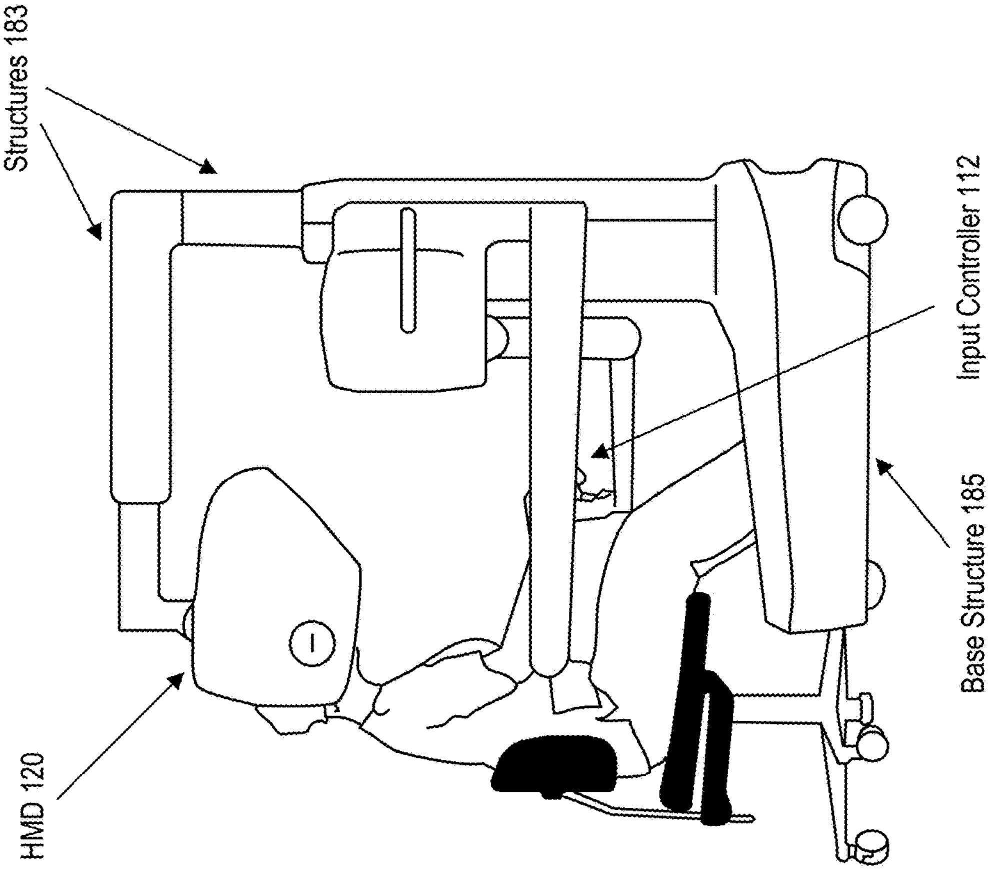

FIG. 5B-5C depict another example of block diagrams of a console 550 and a console 560 for a grounded virtual portal, in accordance with embodiments of the present solution. The console 560 in FIG. 5B can be used for intraoperative procedures, while the console 560 depicted in FIG. 5C can be used for perioperative. Both consoles can provide a grounded HMD 120 and grounded input controllers 112, whereas the locations of the input controllers 112 and HMD 120 can vary. Both examples 550 and 560 can provide structures 183 and linkages 181 that can be used to mount, mechanically couple, connect or relate (e.g., via common grounded reference frames 151) any one or more of: the HMDs 120, the input controllers 112 or any other components of a medical environment 180. The user can adjust the mount associated with the HMD 120 or input controller 112, according to the common frame of reference, which can be also represented and reflected in the virtual space via the HMD 120.

Figure 6:
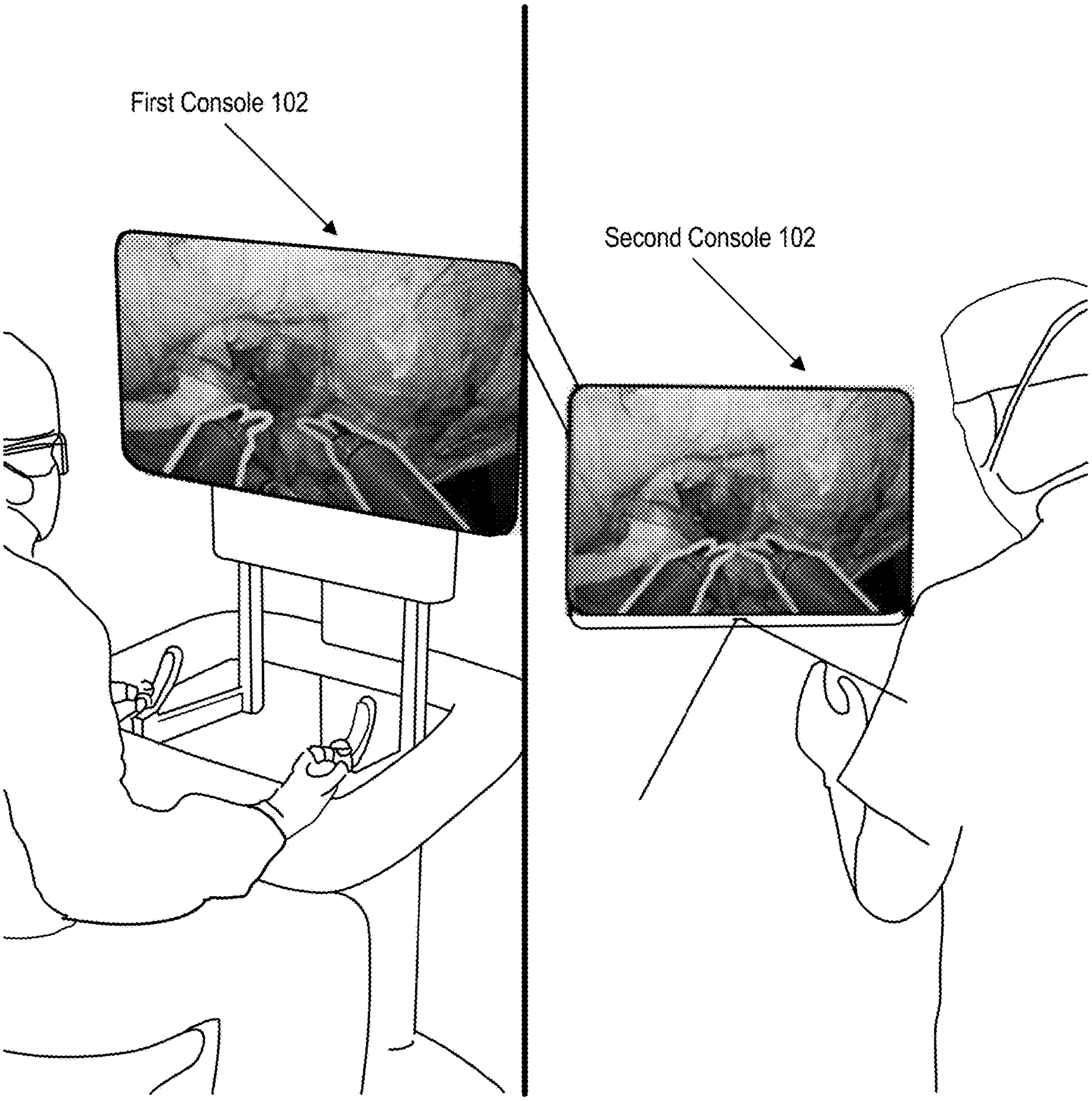
FIG. 6 depicts another example block diagram of a collaborative workspace functionality of a grounded virtual portal, in accordance with an embodiment of the present solution.

FIG. 6 depicts an example 600 of a collaborative workspace functionality of a grounded virtual portal, in accordance with an embodiment of the present solution. A primary surgeon can use a first console 102, while an assistant or secondary surgeon can use a second console 102. Both GVP consoles can present the same or extended reality environment, thereby allowing both surgeons to collaborate on a medical procedure.

Each of the users can utilize respective GVP systems 130 to collaborate in an XR environment. For example, a first computing system 130 and a second computing system 130 can access the same XR environment. While both GVP systems 130 can access and interact with the same XR environment, the manner in which information about the XR environment is conveyed, or the aspects that are conveyed, to each computing system 130 can be dependent on a level of immersion of the computing system 130, ground reference frame, structural aspects of the input controllers (e.g., types of input controllers or types of linkages), or volume of the workspace. In some cases, the input controller 112 can correspond to an input controller, a joystick, or a custom input controller. In some cases, the input controller 112 can be grounded or mechanically coupled to a structure. In some cases, the input controller 112 can be ungrounded. For example, an input controller can include a wearable glove controller (e.g., a sterile wearable surgical controller) that may not be grounded or mechanically fixed to any structure, in which case certain force feedback information or haptic information may not be conveyed to the computing system 130 that utilizes the wearable glove controller. The scaling function, force scalar function, or reference frame can be adjusted, tuned, calibrated or otherwise set based on a role of the user, use case, application, or activity/task/phase of the medical procedure.

Figure 7:
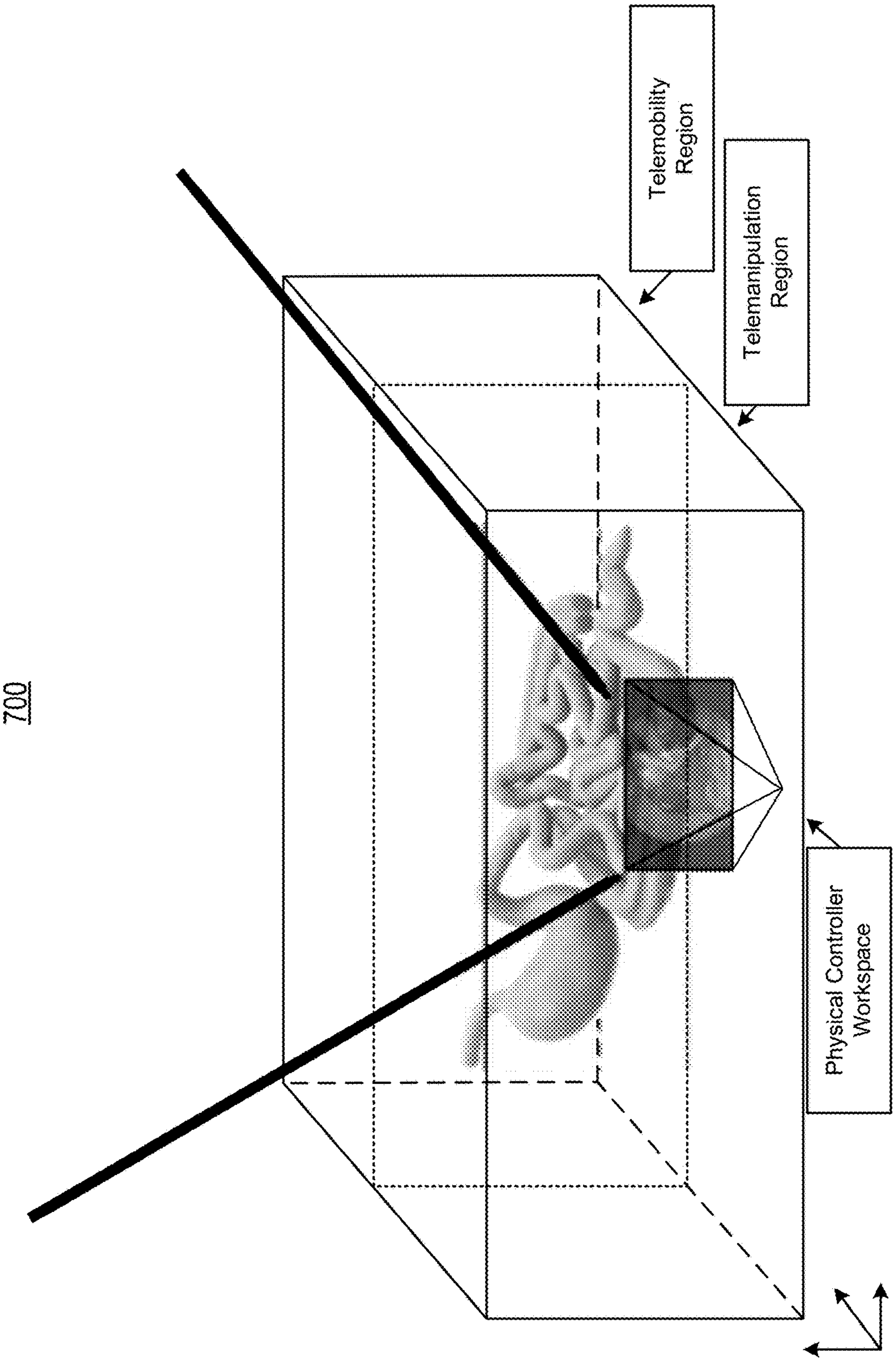
FIG. 7 depicts an example illustration of a workspace along with telemanipulation region and telemobility region.

FIG. 7 depicts an example illustration 700 of a workspace along with telemanipulation region and telemobility region. To provide telemanipulation, the computing system 130 can provide precise input control (e.g., via position-controlled devices). For telemobility, a user can travel larger distances comfortably, without having to constantly clutch due to reaching workspace boundaries and trades off with reduced precision (e.g., via rate-controlled devices). For the computing system 130 console, a single input interface can be provided which dynamically adjusts its motion and scaling properties based on the current context or desired movement of the extended reality user. For example, by understanding the context or intent of a user, the computing system 130 can, while working in a certain physical workspace volume/region with known motion/acceleration, apply specific tuning and properties of the input interface to favor precision of control in telemanipulation tasks. The computing system 130 can determine when a user intends to transition to a telemobility task though specific motion/acceleration or physical position within a workspace and adapt the specific tuning and properties of the input interface to support effective movement in this task.

Figure 8:
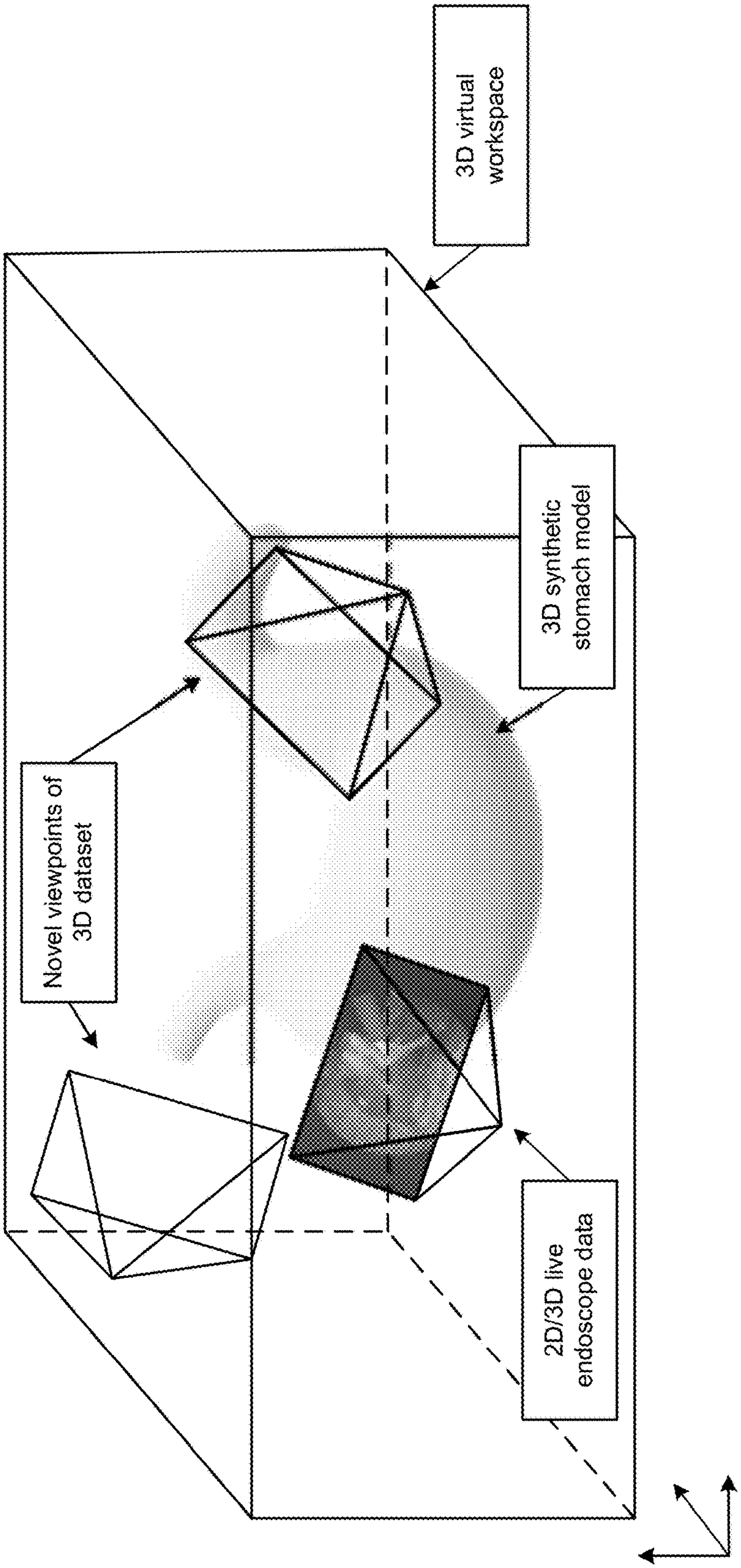
FIG. 8 depicts an example illustration with 3D virtual workspace showing live and synthetic data.

FIG. 8 depicts an example illustration 800 with 3D virtual workspace showing live and synthetic data. To support the telepresence space, the computing system 130 can present information and view perspectives to a remote participant in XR which. For example, if a remote participant is viewing a live/recorded case on an XR HMD, the computing system 130 can dynamically generate additional views/experiences based on live/recorded operating room data (e.g., using a multi-channel file format). For example, an XR viewer could transition between viewpoints during a live case observation from endoscope focused to room focused. For example, in the endoscope focused view, the computing system 130 can provide a 1st person view: View of stereo endoscope video feed that is currently generated. Can scrub through prior video/events independent of the surgeon's current actions. In the endoscope view, the computing system 130 can provide a 3rd person/over the shoulder view in which the computing system 130 dynamically generates a 3D textured map of the workspace (patient interior) using endoscope video and inertial SLAM (kinematics+stereo video). A remote viewer could explore this workspace and scrub through the procedure/movement trajectory of the surgeon, independent of the current actions of the surgeon, to view surgical tool usage, etc. The endoscope focused view can include a beside the surgeon view in which the computing system 130 can use input controller kinematic data and other operating room sensors to generate a viewpoint for a remote XR participant that places them next to the surgeon, allowing them to view the surgeon's hand/foot coordination during key surgical tasks.

The computing system 130 can provide a room focused view that includes 1st person view in which additional sensors in the OR can be used to generate a viewpoint from a tracked personnel/bedside assistant in the operating room which can be presented to a remote XR participant. The computing system 130 can generate the viewpoint based on knowledge of the viewpoint/pose (position and orientation) of the bedside assistant and a dynamically generated OR view synthetically created using point cloud and other sensor data (kinematics, etc.). A remote XR viewer could independently explore the roles of each of the OR staff throughout the duration of a procedure.

The computing system 130 can provide a 3rd person and bird's eye view in which, like the dynamic view generation of 1st person views, the computing system 130 can generate a comprehensive 3D virtual scene using the data recorded during a procedure (kinematics, video, etc.). The computing system 130 can include synthetic virtual environments generated through point cloud or other sensor data, digital twins using kinematics, etc. An XR user would be able to independently navigate this dynamic environment to understand the coordination, workflow, and contributions of each member of the care team before/during/after a procedure.

The computing system 130 can provide a side scrolling view in which the computing system 130 can prioritize comfort for an XR viewer, a side scrolling view would lead a user through a linear representation of the surgical procedure (like a side scrolling video game), highlighting key events or phases of a procedure, after which a user could enter a more engaging view perspective.

Figure 9:
FIG. 9 depicts an example illustration of a 3D virtual illustration of a user in a virtual environment.

FIG. 9 depicts an example illustration 900 of a 3D virtual illustration of a user in an extended reality environment, which can include a virtual environment. The virtual environment can be part of the XR environment. The virtual environment can include objects or people that are a digital twin of objects or people in the physical environment. The computing system 130 can input objects in the virtual environment, which can in-turn control objects in the physical environment.

The computing system 130 can control objects in the extended reality environment depicted in FIG. 9. Objects in the extended reality environment can provide haptic feedback to the computing system 130. The computing system 130 can convey interactions from virtual to physical, and physical to virtual. For example, the computing system 130 can receive an indication that the object in the external reality was moved by a second computing system 130, or physically moved by a person in a medical environment that is captured in the external reality. The computing system 130 can move, in accordance with a scaling function and force scaler function, an input controller of the computing system 130 to reflect the interaction experienced by the object in the medical environment.

In some cases, objects such as the robotic medical system depicted in external reality can be moved via the computing system 130, and movement of the robotic medical system can be depicted in the external reality and corresponding haptic feedback or other force feedback can be provided via the input controller of the computing system 130.

Teams of users can engage with GVP systems 130 to each access the external reality depicted in FIG. 9, and commands from the respective computing system 130 can be reflected and conveyed to each of the other GVP systems 130. The teams of users can include one or more users that are active in the physical medical environment depicted in the external reality environment, in which case interactions by the physical users with objects in the medical environment can be conveyed to each of the users of the GVP systems 130 in a visual manner as well as via force feedback or haptic feedback. Changes to locations of objects can result in changes to ground reference frames, scaling functions, or force scalar functions established for each of the GVP systems 130.

Figure 10A:
FIG. 10A depicts an example illustration of a 3D virtual environment for a training application.

FIG. 10A depicts an example illustration 1000 of a 3D virtual environment for a training application. The 3D virtual environment can be displayed via a user interface on a HMD 120.

Figure 10B:
FIG. 10B depicts an example illustration of an extended reality illustration including a combination of a physical medical environment and a virtual medical environment.

FIG. 10B depicts an example illustration 1030 of an extended reality illustration including a combination of a physical medical environment and a virtual medical environment. The external reality environment can include an endoscope view, a live 3D video view, and a view of the robotic medical system. The external reality environment depicted in FIG. 10B can be used for training applications, intraoperative applications, telesurgery, or telepresence use cases.

Figure 10C:
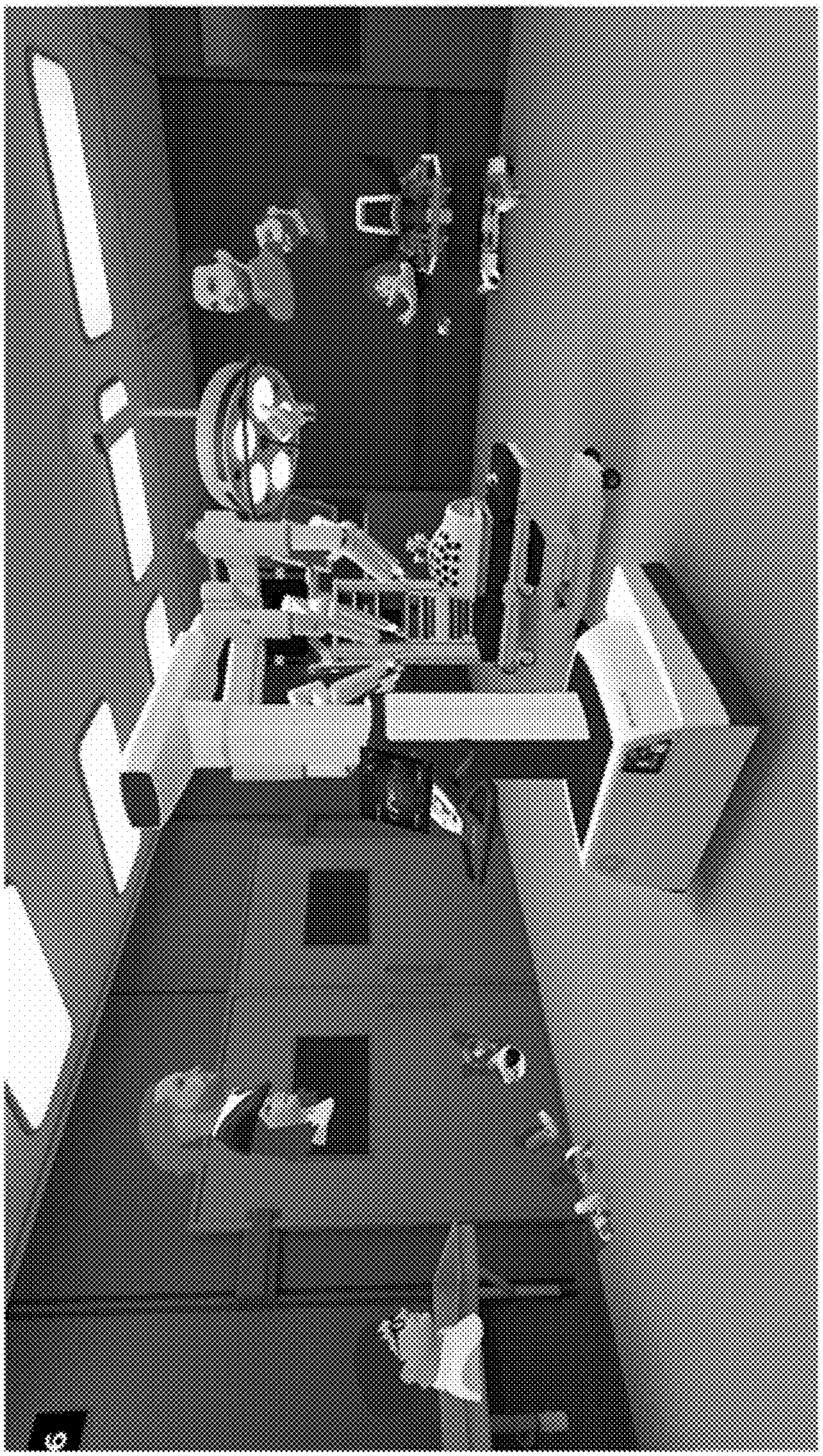
FIG. 10C depicts an example illustration of a tele-proctored virtual simulation of a medical environment.

FIG. 10C depicts an example illustration 1060 of a tele-proctored virtual simulation of a medical environment. FIG. 10C can depict an external reality environment accessed or provided by the computing system 130 for the purposes of simulating a system. The external reality environment of FIG. 10C can simulate one or more components or objects in the medical environment, as well as systems within the medical environment. Multiple users can access the external reality environment depicted in FIG. 10C via respective GVP systems 130 or HMDs in order to interact with or view the system or medical environment. As each user accesses the external reality environment, the renderings of the XR on the respective HMDs and respective input controllers can be provided in accordance with respective scaling functions, force scalar functions, and reference frames. By doing so, the GVP systems 130 can provide for one or more of simulation training, self-led learning in a simulation environment, and coordinated or collaborative training or simulations.

Figure 11:
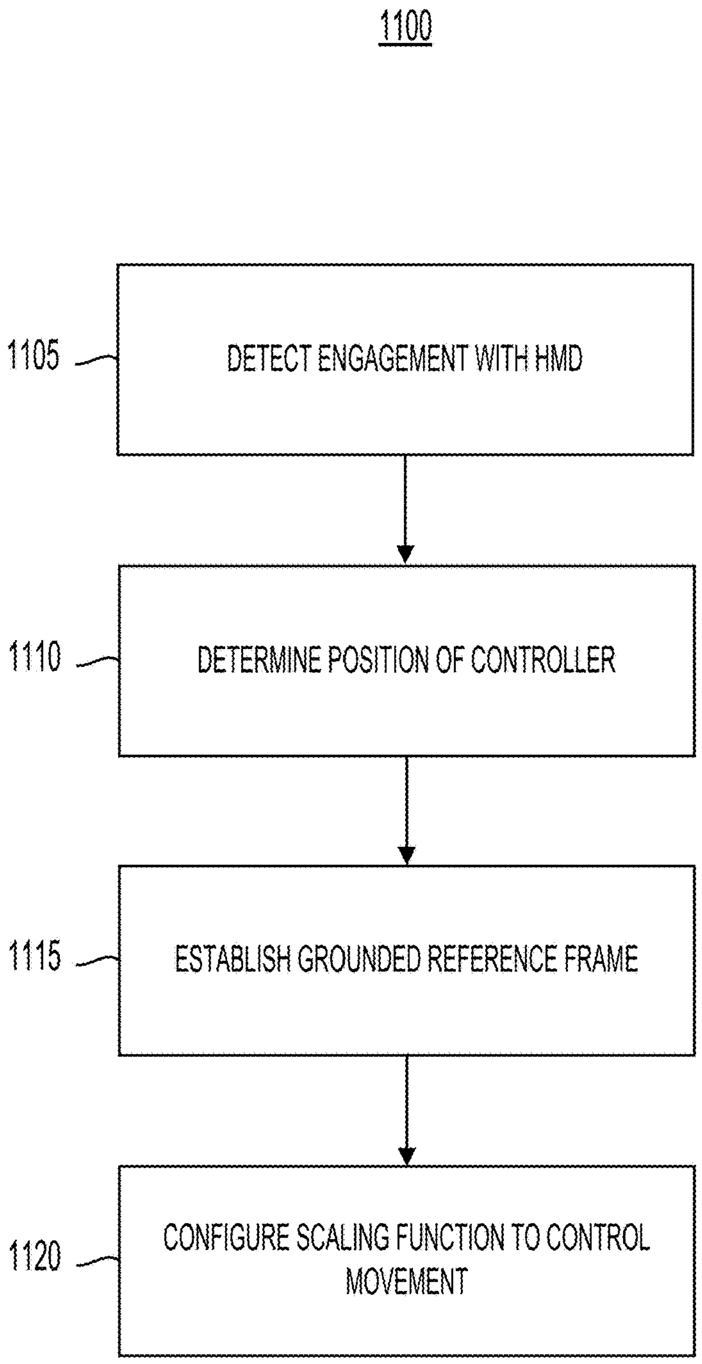
FIG. 11 depicts an example flow diagram of a method of configuring a scaling function based on a grounded reference frame to control a medical tool, in accordance with embodiments of the present solution.

FIG. 11 depicts an example flow diagram of a method 1100 of configuring a scaling function based on a grounded reference frame to control a medical tool, in accordance with embodiments of the present solution. Method 1100 can be a method of interfacing between a grounded virtual portal system and a robotic medical system. Method 1100 can be performed by one or more system or component depicted in FIGS. 1-10C, including, for example, system 100 of FIG. 1 using a computing system 300 of FIG. 3. The procedure can begin at 1105 and end at 1120. At 1105, the method can detect engagement with HMD. At 1110, the method can determine position of controller for medical tool. At 1115, the method can establish grounded reference frame. At 1120, the method can configure scaling function to control movement.

At 1105, the method can detect engagement with HMD. The method can include a grounded virtual portal system detecting, via one or more sensors, an engagement with a head mounted display coupled to a first structure at a first position.

At 1110, the method can determine position of controller for medical tool. The method can include the grounded virtual portal system determining, via the one or more sensors responsive to detection of the engagement, a second position of one or more input controllers. The one or more input controllers can be coupled to a second structure. The one or more input controllers can be configured to control a medical tool of the robotic medical system.

At 1115, the method can establish grounded reference frame. The grounded virtual portal system can establish, based on the first position and the second position, a grounded reference frame for the one or more controllers to be maintained in an extended reality environment rendered via the head mounted display.

At 1120, the method can configure scaling function to control movement. The grounded virtual portal system can configure, based on the grounded reference frame, a scaling function to translate interactions with the one or more input controllers to commands that control at least one of manipulation or movement of the medical tool of the robotic medical system.

Figure 12:
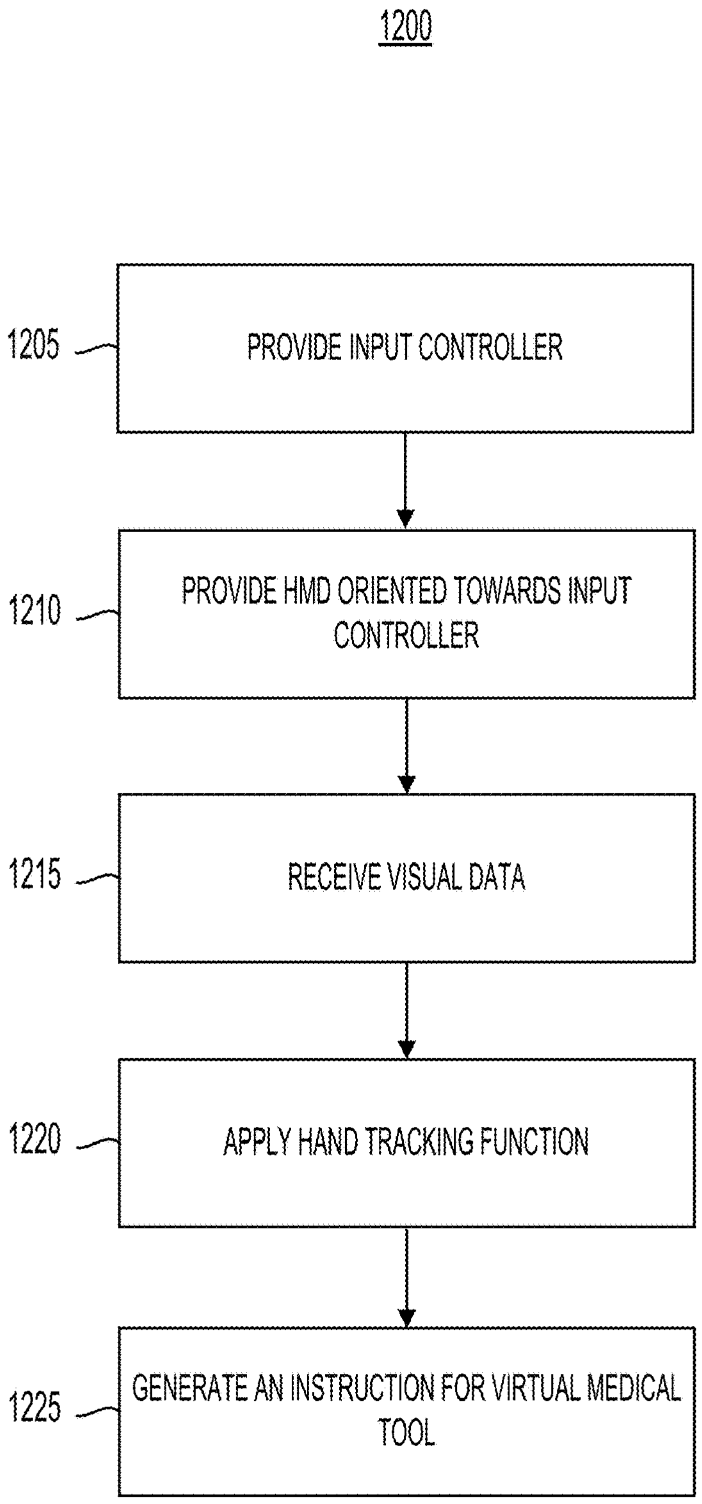
FIG. 12 depicts an example flow diagram of a method of using hand tracking to control a virtual medical tool, in accordance with embodiments of the present solution.

FIG. 12 depicts an example flow diagram of a method 1200 of using hand tracking to control a virtual medical tool, in accordance with embodiments of the present solution. Method 1200 can be performed by one or more system or component depicted in FIGS. 1-10C, including, for example, system 100 of FIG. 1 using a computing system 300 of FIG. 3. The procedure can begin at 1205 and end at 1225. At 1205, the method can provide input controller. At 1210, the method can provide HMD oriented towards an input controller. At 1215, the method can receive visual data. At 1220, the method can apply hand tracking function. At 1225, the method can generate an instruction for a virtual medical tool.

At 1205, the method can provide input controller. The method can provide one or more input controllers coupled to a first structure that is mechanically coupled to a base structure. The one or more input controllers can be configured to control a virtual medical tool of a virtual robotic medical system rendered in an extended reality environment.

At 1210, the method can provide HMD oriented towards an input controller. The method can include providing a head mounted display coupled to a second structure that extends from the base structure. The head mounted display can comprise a camera oriented towards the one or more input controllers.

At 1215, the method can receive visual data. The method can include one or more processors receiving a visual data feed captured by the camera.

At 1220, the method can apply hand tracking function. The method can include the one or more processors applying a hand tracking function to the visual data feed to detect an interaction with the one or more input control.

At 1225, the method can generate an instruction for a virtual medical tool. The one or more processors can generate, based on the interaction detected via application of the hand tracking function, an instruction to control at least one of manipulation or movement of the virtual medical tool of the virtual robotic medical system rendered in the extended reality environment.

Figure 13:
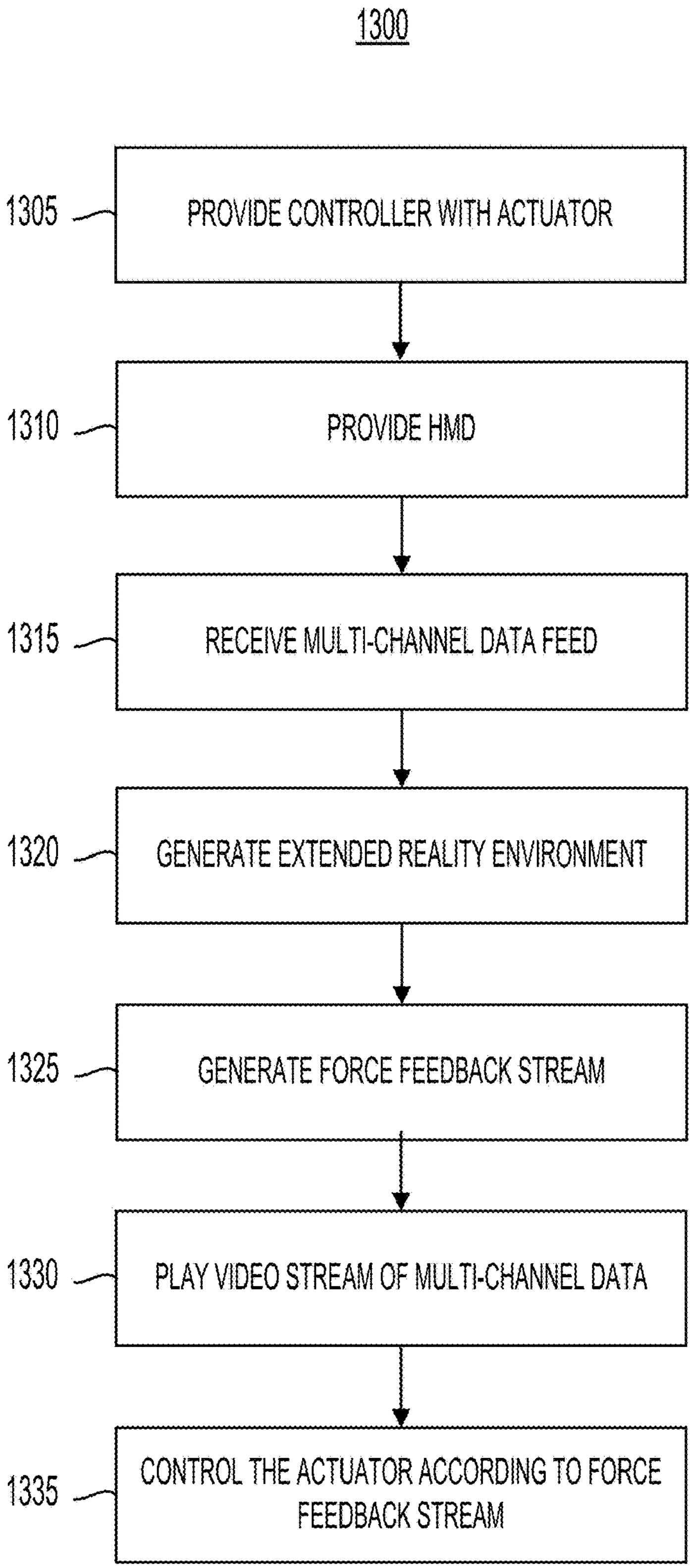
FIG. 13 depicts an example flow diagram of a method of controlling an actuator of a controller of a virtually controlled medical system using a force feedback stream, in accordance with embodiments of the present solution.

FIG. 13 depicts an example flow diagram of a method of controlling an actuator of a controller of a virtually controlled medical system using a force feedback stream, in accordance with embodiments of the present solution. Method 1300 can be performed by one or more system or component depicted in FIGS. 1-10C, including, for example, system 100 of FIG. 1 using a computing system 300 of FIG. 3. The procedure can begin at 1305 and end at 1335. At 1305, the method can provide a controller with an actuator. At 1310, the method can provide an HMD. At 1315, the method can receive a multi-channel data feed. At 1320, the method can generate extended reality environment. At 1325, the method can generate force feedback stream. At 1330, the method can play video stream of multi-channel data. At 1335, the method can control the actuator according to force feedback system.

At 1305, the method can provide a controller with an actuator. The method can provide one or more controllers coupled to a first structure. The first structure can be mechanically coupled to a base structure. The one or more controllers can include an actuator to move the one or more controllers.

At 1310, the method can provide an HMD. The method can provide a head mounted display coupled to a second structure that extends from the base structure.

At 1315, the method can receive a multi-channel data feed. One or more processors coupled with memory can receive a multi-channel data feed of a medical procedure performed via a physical robotic medical system comprising a physical medical tool.

At 1320, the method can generate extended reality environment. The one or more processors can generate, from the multi-channel data feed, an extended reality environment. The extended reality environment can comprise a virtual robotic medical system corresponding to the physical robotic medical system and a virtual medical tool corresponding to the physical medical tool.

At 1325, the method can generate force feedback stream. The method can include the one or more processors generating, from the multi-channel data feed, a force feedback stream.

At 1330, the method can play video stream of multi-channel data. The method can include the one or more processors playing a video stream of the multi-channel data feed via the extended reality environment rendered by the head mounted display.

At 1335, the method can control the actuator according to force feedback system. The method can include the one or more processors controlling the actuator of the one or more controllers in accordance with the force feedback stream and in synchronization with the video stream played by the head mounted display.

Figure 15:
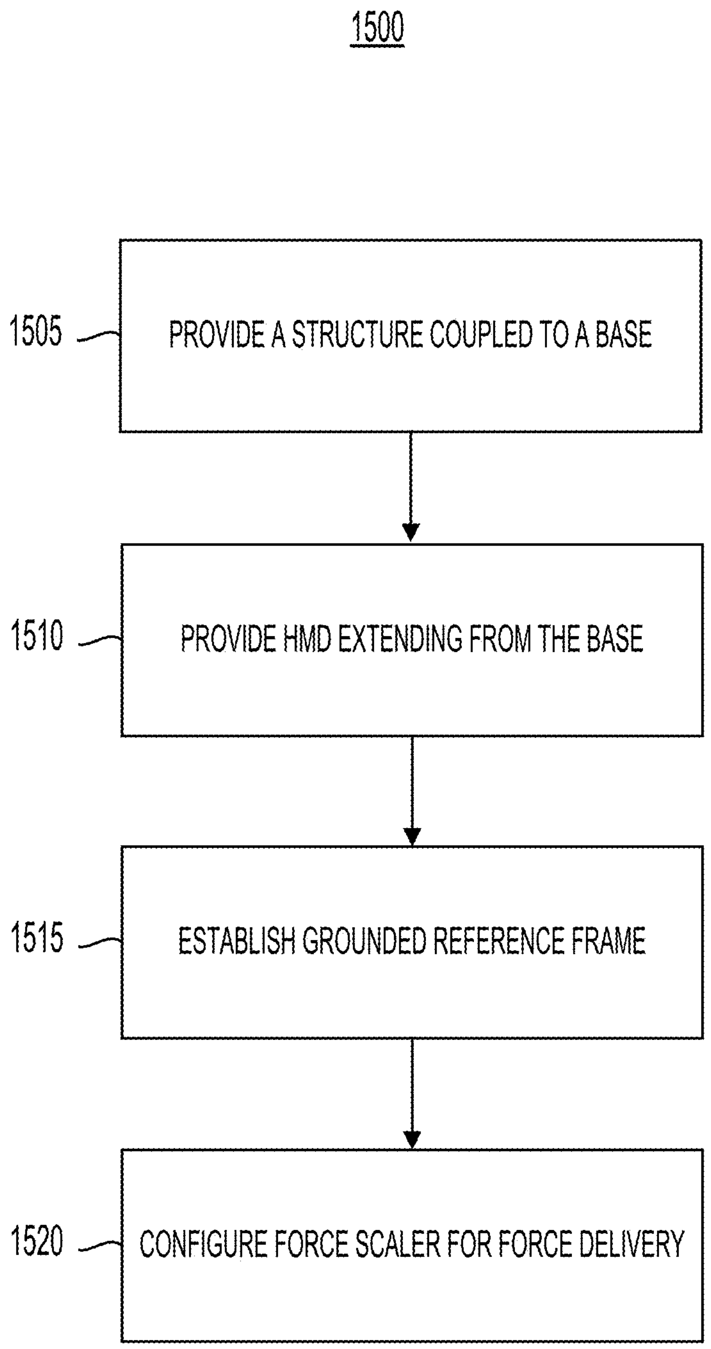
FIG. 15 depicts an example flow diagram of a method of providing a force feedback to an input controller based on the plurality of linkages, in accordance with embodiments of the present solution.

FIG. 15 depicts an example flow diagram of a method 1500 of providing a force feedback to an input controller based on the plurality of linkages, in accordance with embodiments of the present solution. Method 1500 can be performed by one or more system or component depicted in FIGS. 1-10C, including, for example, system 100 of FIG. 1 using a computing system 300 of FIG. 3. The procedure can begin at 1505 and end at 1520. At 1505, the method can provide a structure coupled to a base. At 1510, the method can provide HMD extending from the base. At 1515, the method can establish a grounded reference frame. At 1520, the method can configure force scaler for force delivery.

At 1505, the method can provide a structure coupled to a base. The method can include providing an input controller coupled, via a plurality of linkages, to a first structure. The first structure can be mechanically coupled to a base structure. One or more linkages can interconnect one or more structures. The one or more linkages and the one or more structures interconnected via one or more linkages can be based on or mounted to a base structure. One or more controllers can be configured to control an object of a medical environment. The one or more linkages of the plurality of linkages can include one or more (e.g., a plurality of) degrees of freedom. The degrees of freedom for the linkages can be constrained by one or more constraints or constraint parameters.

At 1510, the method can provide HMD extending from the base. The method can include providing a head mounted display coupled to a second structure. The second structure can extend from the base structure. The head mounted display can be configured to render an extended reality environment corresponding to the medical environment. The head mounted display can be mechanically coupled to the first structure. The object can be a medical tool of a robotic medical system located in the medical environment. The object can be, or correspond to, a virtual object. The medical environment can be, or correspond to, a virtual reality environment.

At 1515, the method can establish a grounded reference frame. The method can include establishing, by one or more processors, coupled with memory, a grounded reference frame for the input controller to be maintained in the extended reality environment rendered via the head mounted display. The one or more processors can apply a constraint to the linkage to limit an amount of movement in a degree of freedom for the linkage. The one or more processors can select the constraint based on a type of the linkage. The type of the linkage can correspond to at least one of a boom-mount, a cart-mount, or a floor-mount system. The one or more processors can select the constraint based on a dimension of a workspace comprising the input controller. The one or more processors can select the constraint based on a dimension of the medical environment in the extended reality environment. The one or more processors can select the constraint in accordance with a degree of freedom of a medical tool of a robotic medical system in the medical environment.

The method can include one or more cameras coupled to the head mounted display and orientated towards the input controller. The one or more processors can be configured to receive data captured from the one or more cameras and determine interactions with the input controller based on the data captured from the one or more cameras. The one or more processors can receive a visual data feed captured by the one or more cameras. The one or more processors can apply a hand tracking function to the visual data feed to detect the interactions with the input controller. The one or more processors can generate, based on the interactions detected via application of the hand tracking function, an instruction to control at least one of manipulation or movement of the object.

At 1520, the method can configure force scaler for force delivery. The method can include configuring, by the one or more processors, based on the plurality of linkages and the grounded reference frame, a force scaler function for bidirectional force delivery between the input controller and the object of the medical environment. The one or more processors can select the force scaler function based on at least one of a task, a phase, or an activity performed in the medical environment. The one or more processors can select the force scaler function based on a profile of a user engaged with the head mounted display. The one or more processors can select the force scaler function based on a profile of a user engaged with the head mounted display. The force scaler function can include a spatial filter configured to map interactions with the input controller to spatially smooth motion of the object.

The one or more processors can detect a transition in a level of immersion of the extended reality environment. The one or more processors can adjust, responsive to the detection of the transition in the level of immersion of the extended reality environment, a parameter of the force scaler function. The one or more processors can detect a change in at least one of a task, activity or phase associated with a procedure performed in the medical environment. The one or more processors can transition, responsive to the detection of the change, a level of immersion of the extended reality environment. The one or more processors can adjust, responsive to the transition in the level of immersion of the extended reality environment, a parameter of the force scaler function.

The one or more processors can detect a transition in a level of immersion of the extended reality environment. The one or more processors can apply a constraint to an amount of movement in one or more degrees of freedom of at least one of the input controller or a linkage of the plurality of linkages. The one or more processors can detect a change in at least one linkage of the plurality of linkages. The one or more processors can adjust the force scaler function responsive to the detection in the change in the at least one linkage. The one or more processors can detect an addition to, or removal from, the plurality of linkages. The one or more processors can adjust the force scaler function responsive to the detection in the addition or the removal.

The one or more processors can receive multi-channel data feed of a medical procedure performed in the medical environment via a physical robotic medical system comprising the object. The object can include a physical medical tool. The one or more processors can generate, from the multi-channel data feed, the extended reality environment comprising a virtual robotic medical system corresponding to the physical robotic medical system and a virtual medical tool corresponding to the physical medical tool.

The one or more processors can generate, from the multi-channel data feed, a force feedback stream. The one or more processors can play a video stream of the multi-channel data feed via the extended reality environment rendered by the head mounted display. The one or more processors can control an actuator of the input controller in accordance with the force feedback stream translated based on the force scaler function, and in synchronization with the video stream played by the head mounted display.

The multi-channel data feed can include the video stream, an event stream recorded by the physical robotic medical system, an environment characteristics associated with the medical procedure performed via the physical robotic medical system, and a kinematics stream captured by the physical robotic medical system. The one or more processors can select, based on a mode, a level of fidelity with which to play the force feedback stream, wherein the mode is one of intraoperative, case review, training, or sales. The one or more processors can actuate the input controller in accordance with the selected level of fidelity.

Figure 16:
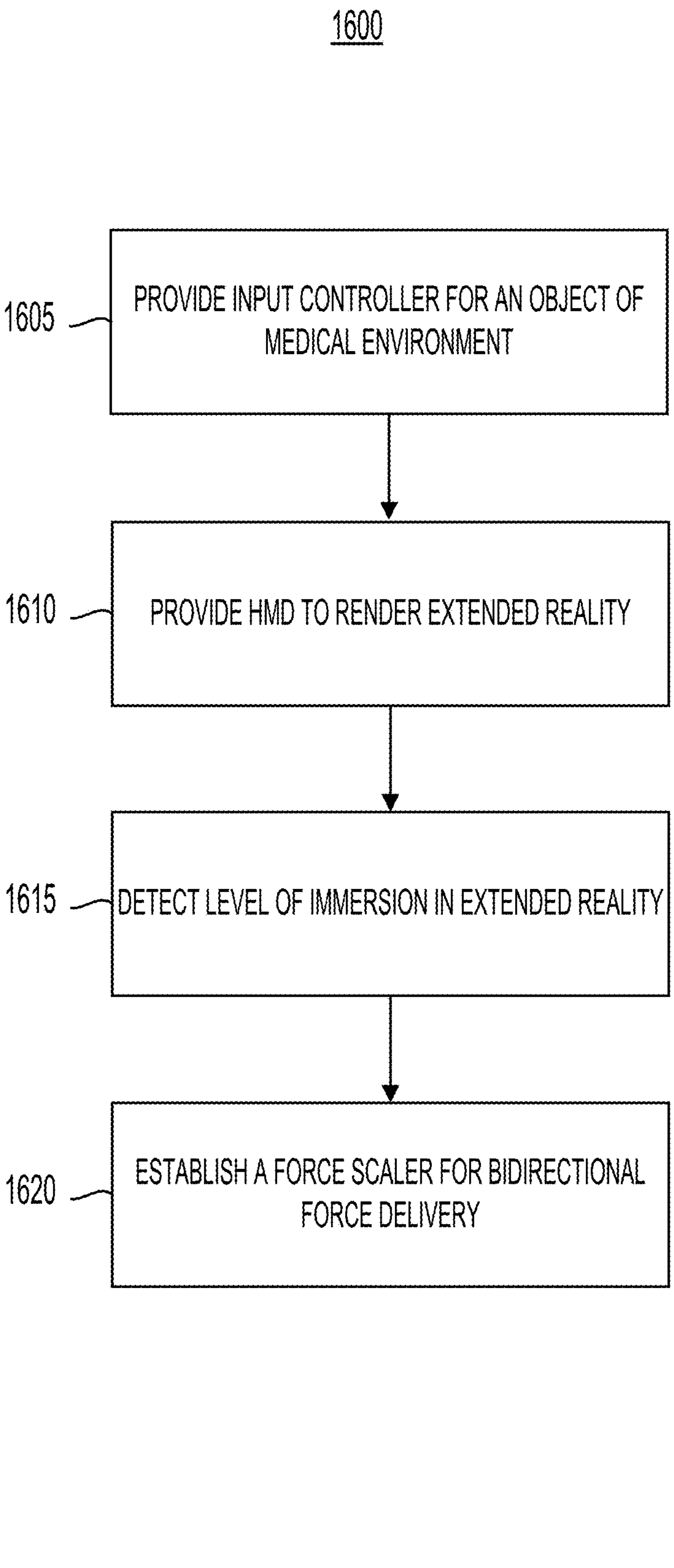
FIG. 16 depicts an example flow diagram of a method of establishing a force scaler according to a level of immersion in an extended reality environment, in accordance with embodiments of the present solution.

FIG. 16 depicts an example flow diagram of a method 1600 of establishing a force scaler according to a level of immersion in an extended reality environment, in accordance with embodiments of the present solution. Method 1600 can be performed by one or more system or component depicted in FIGS. 1-10C, including, for example, system 100 of FIG. 1 using a computing system 300 of FIG. 3. The procedure can begin at 1605 and end at 1620. At 1605, the method can provide input controller for an object of medical environment. At 1610, the method can provide HMD to render extended reality. At 1615, the method can detect level of immersion in extended reality. At 1620, the method can establish a force scaler for bidirectional force delivery.

At 1605, the method can provide input controller for an object of medical environment. The method can include providing an input controller coupled to a first structure. The first structure can be mechanically coupled to a base structure. The input controller can be configured to control an object of a medical environment.

At 1610, the method can provide HMD to render extended reality. The method can include providing a head mounted display coupled to a second structure. The second structure can extend from the base structure. The head mounted display can be configured to render an extended reality environment corresponding to the medical environment.

At 1615, the method can detect level of immersion in extended reality. The method can include detecting, by one or more processors coupled with memory, a level of immersion in the extended reality environment.

At 1620, the method can establish a force scaler for bidirectional force delivery. The method can include establishing, by the one or more processors, in accordance with the level of immersion in the extended reality environment, a force scaler function for bidirectional force delivery between the input controller and the object of the medical environment.

Figure 17:
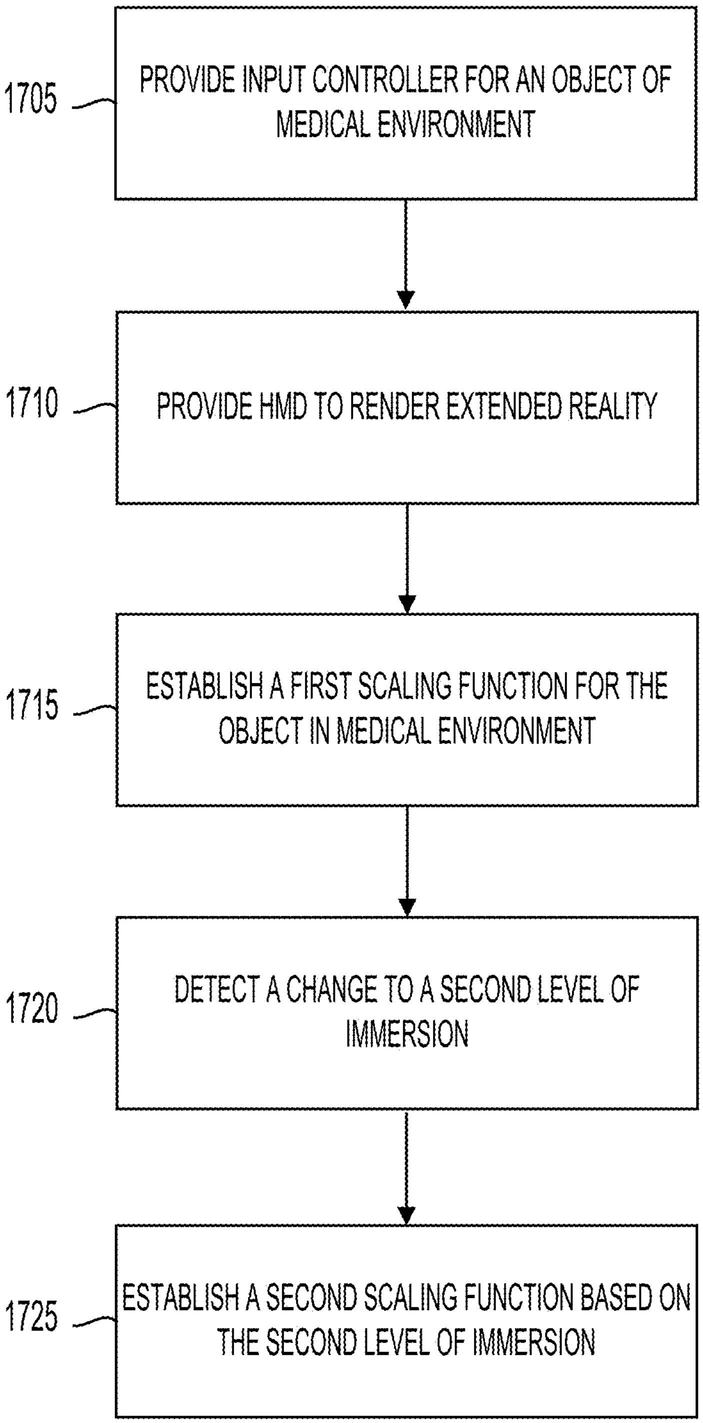
FIG. 17 depicts an example flow diagram of a method of establishing a scaling function according to a level of immersion in an extended reality environment, in accordance with embodiments of the present solution.

FIG. 17 depicts an example flow diagram of a method 1700 of establishing a scaling function according to a level of immersion in an extended reality environment, in accordance with embodiments of the present solution. Method 1700 can be performed by one or more system or component depicted in FIGS. 1-10C, including, for example, system 100 of FIG. 1 using a computing system 300 of FIG. 3. The procedure can begin at 1705 and end at 1725. At 1705, the method can provide input controller for an object of medical environment. At 1710, the method can provide HMD to render extended reality. At 1715, the method can establish a first scaling function for the object in medical environment. At 1720, the method can detect a change to a second level of immersion. At 1725, the method can establish a second scaling function based on the second level of immersion.

At 1705, the method can provide input controller for an object of medical environment. The method can include providing an input controller coupled to a first structure that is mechanically coupled to a base structure. The input controllers can be configured to control an object of a medical environment.

At 1710, the method can provide HMD to render extended reality. The method can include providing a head mounted display coupled to a second structure that extends from the base structure. The head mounted display can be configured to render an extended reality environment corresponding to the medical environment.

At 1715, the method can establish a first scaling function for the object in medical environment. The method can include establishing a first scaling function to translate interactions with the input controller to commands that control at least one of manipulation or movement of the object in the medical environment.

At 1720, the method can detect a change to a second level of immersion. The method can include detecting a change from the first level of immersion rendered in the extended reality environment to a second level of immersion corresponding to virtual reality.

At 1725, the method can establish a second scaling function based on the second level of immersion. The method can include establishing a second scaling function based on the second level of immersion.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

With respect to the use of plural or singular terms herein, those having skill in the art can translate from the plural to the singular or from the singular to the plural as is appropriate to the context or application. The various singular/plural permutations can be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description can illustrate a specific order of method steps, the order of such steps can differ from what is depicted and described, unless specified differently above. Also, two or more steps can be performed concurrently or with partial concurrence, unless specified differently above. Such variation can depend, for example, on the software and hardware systems chosen and on designer choice. All such variations are within the scope of the disclosure. Likewise, software implementations of the described methods can be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). It will be further understood by those within the art that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or can be acquired from practice of the disclosed implementations. It is intended that the scope of the invention be defined by the claims appended hereto and their equivalents.

What is claimed is:

1. A system, comprising:

an input controller coupled, via a plurality of linkages, to a first structure that is mechanically coupled to a base structure, the input controller configured to control an object of a medical environment;

a head mounted display coupled to a second structure that extends from the base structure, the head mounted display configured to render an extended reality environment corresponding to the medical environment; and one or more processors, coupled with memory, to:

establish a grounded reference frame for the input controller to be maintained in the extended reality environment rendered via the head mounted display; and configure, based on a representation of the plurality of linkages and in relation to the grounded reference frame, a force scaler function for bidirectional force delivery between the input controller and the object of the medical environment.

2. The system of claim 1, wherein a linkage of the plurality of linkages comprises a plurality of degrees of freedom, and the one or more processors are further configured to:

apply a constraint to the linkage to limit an amount of movement in a degree of freedom.

3. The system of claim 2, wherein the one or more processors are further configured to:

select the constraint based on a type of the linkage, the type of the linkage corresponding to at least one of a boom-mount, a cart-mount, or a floor-mount system.

4. The system of claim 2, wherein the one or more processors are further configured to:

select the constraint based on a dimension of a workspace comprising the input controller.

5. The system of claim 2, wherein the one or more processors are further configured to:

select the constraint based on a dimension of the medical environment in the extended reality environment.

6. The system of claim 2, wherein the one or more processors are further configured to:

select the constraint in accordance with a degree of freedom of a medical tool of a robotic medical system in the medical environment.

7. The system of claim 1, wherein the one or more processors are further configured to:

select the force scaler function based on a type of medical procedure performed in the medical environment.

8. The system of claim 1, wherein the one or more processors are further configured to:

select the force scaler function based on at least one of a task, a phase, or an activity performed in the medical environment.

9. The system of claim 1, wherein the one or more processors are further configured to:

select the force scaler function based on a profile of a user engaged with the head mounted display.

10. The system of claim 1, wherein the one or more processors are further configured to:

select the force scaler function based on a profile of a user engaged with the head mounted display.

11. The system of claim 1, wherein the force scaler function comprises a spatial filter configured to map interactions with the input controller to spatially smooth motion of the object.

12. The system of claim 1, wherein the one or more processors are further configured to:

detect a transition in a level of immersion of the extended reality environment; and adjust, responsive to the detection of the transition in the level of immersion of the extended reality environment, a parameter of the force scaler function.

13. The system of claim 1, wherein the one or more processors are further configured to:

detect a change in at least one of a task, activity or phase associated with a procedure performed in the medical environment;

transition, responsive to the detection of the change, a level of immersion of the extended reality environment; and adjust, responsive to the transition in the level of immersion of the extended reality environment, a parameter of the force scaler function.

14. The system of claim 1, wherein the one or more processors are further configured to:

detect a transition in a level of immersion of the extended reality environment; and
reality environment; and apply a constraint to an amount of movement in one or more degrees of freedom of at least one of the input controller or a linkage of the plurality of linkages.

15. The system of claim 1, wherein the one or more processors are further configured to:

detect a change in at least one linkage of the plurality of linkages; and adjust the force scaler function responsive to the detection in the change in the at least one linkage.

16. The system of claim 1, wherein the one or more processors are further configured to:

detect an addition to, or removal from, the plurality of linkages; and adjust the force scaler function responsive to the detection in the addition or the removal.

17. The system of claim 1, wherein the head mounted display is mechanically coupled to the first structure, and the object is a medical tool of a robotic medical system located in the medical environment.

18. The system of claim 1, wherein the object is a virtual object, and the medical environment is a virtual reality environment.

19. The system of claim 1, comprising:

one or more cameras, coupled to the head mounted display, orientated towards the input controller; and the one or more processors further configured to:

receive data captured from the one or more cameras; and determine interactions with the input controller based on the data captured from the one or more cameras.

20. The system of claim 19, wherein the one or more processors are further configured to:

receive a visual data feed captured by the one or more cameras;

apply a hand tracking function to the visual data feed to detect the interactions with the input controller; and generate, based on the interactions detected via application of the hand tracking function, an instruction to control at least one of manipulation or movement of the object.

21. The system of claim 1, wherein the one or more processors are further configured to:

receive multi-channel data feed of a medical procedure performed in the medical environment via a physical robotic medical system comprising the object, wherein the object comprises a physical medical tool;

generate, from the multi-channel data feed, the extended reality environment comprising a virtual robotic medical system corresponding to the physical robotic medical system and a virtual medical tool corresponding to the physical medical tool;

generate, from the multi-channel data feed, a force feedback stream;

play a video stream of the multi-channel data feed via the extended reality environment rendered by the head mounted display; and control an actuator of the input controller in accordance with the force feedback stream translated based on the force scaler function, and in synchronization with the video stream played by the head mounted display.

22. The system of claim 21, wherein the multi-channel data feed comprises:

the video stream;

an event stream recorded by the physical robotic medical system;

environment characteristics associated with the medical procedure performed via the physical robotic medical system; and a kinematics stream captured by the physical robotic medical system.

23. The system of claim 21, wherein the one or more processors are further configured to:

select, based on a mode, a level of fidelity with which to play the force feedback stream, wherein the mode is one of intraoperative, case review, training, or sales; and actuate the input controller in accordance with the selected level of fidelity.

24. A method, comprising:

providing an input controller coupled, via a plurality of linkages, to a first structure that is mechanically coupled to a base structure, the input controller configured to control an object of a medical environment;

providing a head mounted display coupled to a second structure that extends from the base structure, the head mounted display configured to render an extended reality environment corresponding to the medical environment;

establish, by one or more processors coupled with memory, a grounded reference frame for the input controller to be maintained in the extended reality environment rendered via the head mounted display; and configuring, by the one or more processors, based on a representation of the plurality of linkages in relation to the grounded reference frame, a force scaler function for bidirectional force delivery between the input controller and the object of the medical environment.

25. A non-transitory computer-readable medium storing processor-executable instructions that, when executed by one or more processors, cause the one or more processors to:

establish a grounded reference frame for an input controller to be maintained in an extended reality environment rendered via a head mounted display, wherein:

the input controller is coupled, via a plurality of linkages, to a first structure that is mechanically coupled to a base structure, the input controller is configured to control an object of a medical environment, the head mounted display is coupled to a second structure that extends from the base structure, the head mounted display is configured to render the extended reality environment corresponding to the medical environment; and configure, based on a representation of the plurality of linkages in relation to the grounded reference frame, a force scaler function for bidirectional force delivery between the input controller and the object of the medical environment.

* * * * *